United States Patent [19]
Minion et al.

[11] Patent Number: 6,162,435
[45] Date of Patent: Dec. 19, 2000

[54] RECOMBINANT MYCOPLASMA HYOPNEUMONIAE VACCINE

[75] Inventors: F. Chris Minion, Ames, Iowa; Tsungda Hsu, Bronx, N.Y.

[73] Assignee: Iowa State University Research Foundation, Inc., Ames, Iowa

[21] Appl. No.: 09/198,484

[22] Filed: Nov. 24, 1998

Related U.S. Application Data

[60] Provisional application No. 60/066,565, Nov. 26, 1997.

[51] Int. Cl.$^7$ .......................... A61K 39/00; A61K 39/02; A61K 9/14; C12Q 1/68; C12P 21/06
[52] U.S. Cl. ...................................... 424/190.1; 424/190.1; 424/264.1; 424/489; 435/6; 435/69.3; 435/340; 530/388.4
[58] Field of Search .............................. 424/190.1, 264.1, 424/489; 435/6, 69.3, 340; 530/388.4

[56] References Cited

U.S. PATENT DOCUMENTS

| | | |
|---|---|---|
| 4,170,646 | 10/1979 | Gustafson et al. . |
| 4,894,332 | 1/1990 | Schaller et al. ........................ 435/69.3 |
| 5,240,706 | 8/1993 | Faulds ....................................... 424/92 |
| 5,252,328 | 10/1993 | Faulds et al. . |
| 5,338,543 | 8/1994 | Fitzgerald et al. . |
| 5,565,205 | 10/1996 | Peterson et al. . |
| 5,712,090 | 1/1998 | Artiushin et al. . |
| 5,788,962 | 8/1998 | Wise et al. ........................... 424/264.1 |

FOREIGN PATENT DOCUMENTS

| | | | |
|---|---|---|---|
| 196251 | 1/1986 | European Pat. Off. | ........ C12N 15/00 |
| WO 9115593 | 10/1991 | WIPO | ............................. C12N 21/00 |

OTHER PUBLICATIONS

F. Chris Minion et al., "Use of an Enhanced *Escherichia coli* Opal Suppressor Strain to Screen a *Mycoplasma hyopneumoniae* Library", FEMS Microbiology Letters, 131, 1995, pp. 81–85.

Tsungda Hsu et al., "Molecular Analysis of the P97 Cilium Adhesin Operon of *Mycoplasma hyopneumoniae*", Gene 11374, 1998, pp. 1–11.

*Primary Examiner*—James O. Housel
*Assistant Examiner*—Ja-Na A. Hines
*Attorney, Agent, or Firm*—Dickstein Shapiro Morin & Oshinsky, LLP

[57] ABSTRACT

A *Mycoplasma hyopneumoniae* protein prepared by recombinant DNA or synthetic means, DNA sequences coding for the protein, an expression vector and transformed host containing the DNA sequences, a vaccine based on the protein, a vaccine based on the DNA sequences, methods of treating swine to prevent enzootic pneumonia using the vaccines, and diagnostic tests based on the protein or antibodies raised against it for detecting the presence of Mhyo infection in swine herds.

17 Claims, 8 Drawing Sheets

```
ATAAAACCCGGAGGTATTTATCCTATGAAGTTAGCAAAATTACTTAAAAAACCTTTTTGATT
AATAACAACAATTGCCGGAATTAGTCTTAGTTTATCAGCCGCTGTTGGTACAGTTGTCGGAA
TTAATTCTTATAATAAATCATATTATTCTTATCTAAATCAGATCCCGAGTCAGCTAAAACTA
GCAAAAAATGCTAAAATTAGTCAGGAAAAATTTGATTCAATTGTTTTAAATCTTAAAATTAA
AGATAATTTTAAAAAATGATCGGCAAAAACAGTTTTAACTGCTGCCAAAAGTGATCTTTATC
GTTATAATCTTGTTTCTGCTTTTGATTTAAGTGAACTAATAAACAATGATTATTTAGTAAGT
TTTGATCTTGAAAATGCAGTAGTTGATCAAAATTCAATTAAAAATGTTGTTATTTATGCAAA
ATCTGATAAGGATCAAATAACTTATTCAAAACAAATTGTACTTAAAGGCTTTGGAAATACAG
AACAAGCTAGAACTAATTTTGATTTTAGTCAAATTGATTCAAGCAAGTCTTTTGTTGATCTT
TCAAGAGCAAATCTAACTTTGATGGAATTCCAAATTTTGCTTGCCCAAAATTTTGAAAATGA
AAGAGGAAGTAATTGATTTTCACGACTTGAAAGAGCTTTGGTTGCATCAAAAGCGAGTCTTT
CACTTTATAATTCCTTAGGAGAACCCGTATTTTTAGGCCCAGATTATCAATTAGACCCACTT
TTGGACCGAAAAAAATTATTAACTTTGTTAAATAAAGATGGAAAATTAGTTCTTGGACTTAA
TTTAGTGCAAATTTCAACTAAAAAAACTATGAATTTAAATCTTGAAGTTCGCGGCGCGATTT
CAAATCAGGAAATTTCTAAAATTCTAAAATCCTGACTTGAAACAAATCTTCAAGGCAAATTA
AAAACCAAAGATGATTTGCAAATGGCACTTGTAAAAGATAAAATTAGCCTCTCTGATTATTG
ATATGGATCTCCGAATTCAAAAGTAAATACATCCCAAATTTTAACAAAAAGTAAAGAATTTA
AAGATCTTTTTGATTTAAGTGAGACAAATTTTTTTCTTAATACCAAAATCGGAACTGTCTAT
TTAAGTATTATTCCCAAACTTTTAGATCCAAGTCAGATTTCTGTTGTTGATAAGAAAAAACT
AGTTGAAAATCAAAAAATTCGCTTTGAAATTACTGCTTCTTTAAAACGAAAAGCTATTGATA
AAAAATTTATCATCCAGGATCTTCCAGTTTTTGTTGATCTAAAAGTTGATTTTAATAAATAC
CAAGCCGCTGTTGCCCAAATGTTTGGAACGATAAAAGCAGTTAAAGAATTTTCAATGCCTGA
AGATCAAGATGCAAAAACTTTATCCTCAAATGAAATAAAACAGCGAGTTGATCGACTTTTTG
AACTAGCAAAAACAGTGACTAATTTGGAAAATCCAAGTGAAGAAGTTCTTAAAAGCATTTAT
TTATTAAATACGGGAAAATATTTAGTCGACCAAGACCAGGAAAAAGTAAAACAAGAGCTAAA
AACCGTGATTGAGGGCTTAAAATCAAAGGCAAATACTCAAAAAACAGAAAAAAATAGCCCCA
CACAACCGAAAAAAACCAGAGGTTTCACTAGCTAAAACAACAGAAAATTCAGCAAAAACACTC
AAGGTAAGCACTTTTGCAGAAGAAGCTAAGGGTCAAAGTCAAAGTCAGCAAACACAACCAGT
TTCCACTTCATCGCCTCAAACTAGTCAAAATTCACTTCCTAATTCCACAAGCAGCTCAAATT
CTGTATTAGAAAATGAAAAATTTGGGACAAGCATTTGAACAGCTTTTAATTTCGCTAATATT
TATAATCTTGAAAATACAAAAAGCGAATATGAGATCTCAACTTTAGGAAATAAGCTATTTTT
TGATTTTAAATTAGTTGATAAAACTAATCAAAATCTAATTTTGGCTCAGTCCAAAATTACTC
TTAATAATATTATTAATTCTAATAAATCTGCCTATGATATAATTAAGAAATTCAATCCCCAT
GTGTTTTTAGATGGAACAATTAATTATCAAAATCAAGGAAAAGATAAAAAAGAATTTATCCT
AAAAGATTTAAGTGATAATAAATTAATATTTAAATCAGAAGATGCAATTCAAACTGATCAAG
GTTTAGAGCTAAAGAAACCTTTGAAATTACAGTCAAAATCGTCTAATCCAGAAAAAGAAATA
TCAACTTCTTTATATACCGGAGCAATTTATTTAGTTTTTGATGCAAAAAATATTTCCGATGG
TAATTGGATTAATCTTTTAGCCGATAGAAAAGGAAAAGGGCTTGTAATTAAAGTTCAAAATT
CAAATAATAATGTACCTAAAACCAAAGAAATTGTTGAGAATGGTACCTATTTATATGAAATT
CTTGCTGGCAAGGATTCGATTAAGGTAAATTCTTATTTTTTTCCAACAAAGTACCCAAAACG
TGTAAAACGTCTTAAATTCGAGATTAACCCTAAAGACACCTTGCCAAATTTCTTTACTTTAG
AATGATTTCATCTTGATTGGTATCAAATCGGCCCAGGCGAACAAAATAAAAAACCACAACAA
AACGCTAAAAAAGAACCTACAATTATATTAAAAACGCTGGCAATATTTAATGATAAATCATT
TGCAGAGAAAGGAAGTTTAACAAAAAGAAGTGAATTAATTAACGGGTTGATTAGAAACTATG
TTAAAAAGTAACGATCAAATTTTTGTTAAAAA
```

```
P102    MKLAKLLKKPFWLITTIAGISLSLSAAVGTVVGINSYNKSYYSYLNQIPS
1232/3  MKLAKLLKKPFWLITTIAGISLSLSAAVGTVVGINSYNKSYYSYLNQIPS
2166         LLKKPFWLITTIAGISLSLSAAVGIVVGINSYNKSYYSYLNENPS
1234    MKLAKLLKKPFWLITTIAGISLSLSAAVGTVVGINSYNKSYYSYLNENPS

P102    QLKVAKNAKISQEKFDSIVLNLKIKDNFKKWSAKTVLTAAKSDLYRYNLV
1232/3  QLKVAKNAKISQEKFDSIVLNLKIKDNFKKWSAKTVLTAAKSDLYRYNLV
2166    QLKTTKTTKISQQDFDKIVSNLKIRDNFKKISAKTALSAVKNDLYRYDLV
1234    QLKTTKTTKISQQDFDKIVSNLKIRDNFKKISAKTALSAVKNDLYRYDLV

P102    SAFDLSELINNDYLVSFDLENAVVDQNSIKNVVIYAKSDKDQITYSKQIV
1232/3  SAFDLSELINNDYLVSFDLENAVVDQNSIKNVVIYAKSDKDQITYSKQIV
2166    RAFEFSSLETNNYQISFDLENAVVDQNSIKNVVIYAKSDKDQITYSKQIV
1234    RAFEFSSLETNNYQISFDLENAVVDQNSIKNVLVFAKSEKDQVTYSKQIE

P102    LKGFGNTEQARTNFDFSQIDSSKSFVDLSRANLTLMEFQILLAQNFENER
1232/3  LKGFGNTEQARTNFDFSQIDSSKSFVDLSRANLTLTEF..........
2166    LKGFGNTEQARTNFDFSQIDSSKSFVDLSRANLTLTEFQILLAQNFENER
1234    LKGFAQDDEAAGDLVKFQIDQRKSFVNLYKFDYSFSEFQRI

P102    GSNWFSRLERALVASKASLSLYNSLGEPVFLGPDYQLDPVLDRKKLLTLL
1232/3  ..........................................
2166    GSNWFSRLERALVASKASLSLYNSLGEPVFLGPDYQLDPVLDRKKLLTLL
```

RECOMBINANT MYCOPLASMA HYOPNEUMONIAE VACCINE

This application claims the benefit of U.S. Provisional Application No. 60/066,565 filed Nov. 26, 1997, which is herein incorporated by reference.

FIELD OF THE INVENTION

The present invention relates to Mycoplasma hyopneumoniae (M. hyopneumoniae or Mhyo) and more particularly to an antigenic Mhyo protein. Still more particularly, this invention relates to a vaccine for protecting against enzootic pneumonia, and in particular enzootic pneumonia in swine.

BACKGROUND OF THE INVENTION

Enzootic pneumonia in swine, also called mycoplasmal pneumonia, is caused by Mhyo. The disease is a chronic, non-fatal disease affecting pigs of all ages. Infected pigs show only mild symptoms of coughs and fever, but the disease has significant economic impact due to reduced feed efficiency and reduced weight gain. Enzootic pneumonia is transmitted from pig to pig through the nasal passages by airborne organisms expelled from the lungs of infected pigs. The primary infection by Mhyo may be followed by secondary infection by other mycoplasma species (Mycoplasma hyorhinis and Mycoplasma flocculare) as well as other bacterial pathogens.

Mhyo is a small, prokaryotic microbe capable of a free living existence, although it is often found in association with eukaryotic cells because it has absolute requirements for exogenous sterols and fatty acids. These requirements generally necessitate growth in serum-containing media. Mhyo is bounded by a cell membrane, but not a cell wall. The genome of Mhyo is approximately 1,000,000 base pairs in length.

The physical association of mycoplasmas with the host cell surface is the basis for the development and persistence of enzootic pneumonia. Mhyo infects the respiratory tract of swine, colonizing the trachea, bronchi, and bronchioles. The mycoplasma produces a ciliostatic factor which causes the cilia lining the respiratory passages to stop beating. Eventually, the cilia degenerate, leaving the pig prone to infection by secondary pathogens. Characteristic lesions of purple to gray areas of consolidation are observed in infected animals. Surveys of slaughtered animals revealed lesions in 30 to 80% of swine. Results from 37 herds in 13 states indicated that 99% of the herds had hogs with pneumonia lesions typical of enzootic pneumonia. Therefore, the need for effective preventative and treatment measures are great.

Antibiotics such as tiamulin, trimethoprim, tetracyclines and lincomycin have some benefit, but are expensive and require prolonged use. Additionally, antibiotics have not been shown to effectively eliminate spread or reinfection of Mhyo. Prevention by maintaining pathogen-free herds is sometimes possible but reintroduction of Mhyo often occurs. Due to the serious economic consequences of swine pneumonia, vaccines against Mhyo and diagnostic testing methods which will indicate the presence of an infection have been sought. Vaccines containing preparations of mycoplasmal organisms grown in serum-containing medium have been marketed, but are expensive and raise concerns regarding adverse reactions induced by serum components present in the immunizing material. Other attempts to provide vaccines have not been successful, and the disease remains widespread.

What is needed is a vaccine against mycoplasma infection in swine, and a cost-effective process of producing the same. Also needed is a diagnostic test for detecting the presence of swine mycoplasma infection in swine herds.

SUMMARY OF THE INVENTION

The present invention provides purified or isolated Mycoplasma hyopneumoniae protein P102 prepared by recombinant or synthetic means, and polypeptides or peptides that are portions of P102 and which when administered to a swine elicit the formation of antibodies that bind to Mhyo. Preferred P102 and polypeptides have an amino acid sequence as shown in FIG. 1, or a fragment of such sequence.

Also provided are recombinant DNA molecules useful in preparing P102 and the aforementioned polypeptides. Preferred recombinant DNA molecules are characterized by a DNA sequence selected from the sequence shown in FIG. 2, DNA sequences encoding the amino acid sequences shown in FIGS. 1 and 5, DNA sequences that hybridize to any of those DNA sequences and that code for Mhyo P102, DNA sequences that code for an antigen of Mhyo coded by any of the foregoing DNA sequences, and DNA sequences which are degenerate as a result of the genetic code to the aforementioned DNA sequences and which code for an antigen of Mhyo. Expression vectors and host cells containing the proteins or DNA sequences of the present invention are also provided.

The present invention also includes a vaccine for immunizing swine against Mhyo infections by administering the produced and subsequently isolated P102, polypeptides, or an expression vector containing the DNA sequences of the present invention to swine (e.g., by injection), in an amount sufficient to elicit the formation of antibodies. A diagnostic test based on P102, the polypeptides of the present invention, or antibodies raised against them is also provided for testing swine herds for Mhyo infections.

Additional advantages and features of the present invention will be apparent from the following detailed description, drawings and examples which illustrate preferred embodiments of the invention.

BRIEF DESCRIPTION OF THE DRAWINGS

FIG. 1 depicts the amino acid sequence of P102 (SEQ ID NO: 2).

FIG. 2 depicts the DNA sequence encoding Mhyo P102 (SEQ ID NO: 1).

FIG. 5 depicts the alignment of the translated amino acid sequences of P102 (SEQ ID NO: 2) with the sequences of several clones(SEQ ID NOS 3–5, respectively).

DETAILED DESCRIPTION OF THE PREFERRED EMBODIMENTS

Figure 3:
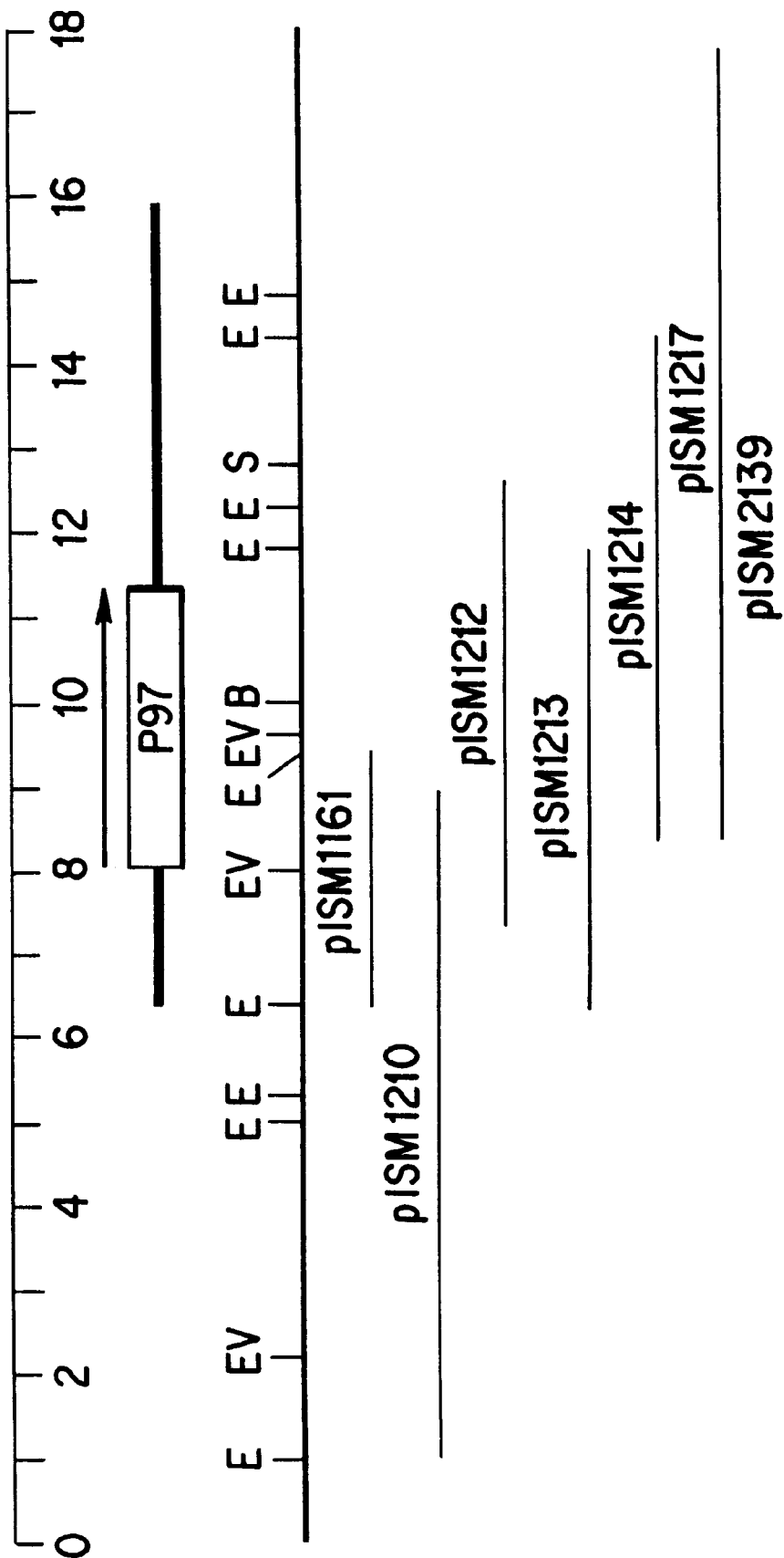
FIG. 3 depicts a restriction map of clones of the P97 operon.

Reference will now be made in detail to the presently preferred embodiments of the invention, which, together with the drawings and the following examples, serve to explain the principles of the invention. These embodiments are described in sufficient detail to enable those skilled in the art to practice the invention, and it is to be understood that other embodiments may be utilized, and that structural and chemical changes may be made without departing from the spirit and scope of the present invention.

The following abbreviations are used in this application: aa, amino acid(s); Ab, antibody(ies); bp, base pair(s); CHEF, clamped homogenous electric field; H., Haemophilus, kb, kilobase(s) or 1000 bp; Kn, kanamycin; LB, Luria-Bertoni media; M., Mycoplasma; mAb, monoclonal Ab; ORF, open reading frame; PCR, polymerase chain reaction; $^R$, resistant/resistance; Tn, transposon(s); ::, novel junction (fusion or insertion). One letter and three letter code designations for amino acids are given in Table 1, below.

TABLE 1

Amino Acid Code Designations

| Amino Acid | Three letter code | One letter code | Amino Acid | Three letter code | One letter code |
|---|---|---|---|---|---|
| Alanine | Ala | A | Leucine | Leu | L |
| Arginine | Arg | R | Lysine | Lys | K |
| Asparagine | Asn | N | Methionine | Met | M |
| Aspartic Acid | Asp | D | Phenylalanine | Phe | F |
| Cysteine | Cys | C | Proline | Pro | P |
| Glutamic Acid | Glu | E | Serine | Ser | S |
| Glutamine | Gln | Q | Threonine | Thr | T |
| Glycine | Gly | G | Tryptophan | Trp | W |
| Histidine | His | H | Tyrosine | Tyr | Y |
| Isoleucine | Ile | I | Valine | Val | V |

The term "protein" used in the following description refers to a microbially expressed protein that has been separated, isolated, or purified from other proteins, whole bacteria, and cellular substances by conventional means such as preparative chromatography, immunological separation, or passage through a metal chelate column. The term "mutant" as used in the following description refers to an amino acid or DNA sequence having minor modifications or conservative variations such that the sequence results in proteins having substantially equivalent function when compared to native Mhyo P102.

The term "conservative variations" denotes the replacement of an amino acid residue by another, biologically similar residue, or the substitution of nucleotides in a DNA sequence to achieve the same result. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The present invention concerns the *Mycoplasma hyopneumoniae* protein P102, in an isolated, purified, and/or recombinant form, and the use of P102, or fragments thereof, as a vaccine or diagnostic tool in swine. P102, which has been shown by the inventors to cause an immunological reaction in swine protected against virulent challenge, has been isolated, characterized, and named by the present inventors. Also within the scope of the present invention are DNA sequences corresponding to recombinant P102, and expression vectors and hosts containing such sequences. A vaccine containing isolated, purified, and/or recombinant P102, or DNA sequences encoding P102 for immunizing swine against Mhyo infections, and a diagnostic tool based on P102 useful in testing swine herds for infections are also provided.

Any Mhyo strain may be used as a starting material to produce the P102 of the present invention. Suitable strains of Mhyo may be obtained from a variety of sources, including depositories such as the American Type Culture Collection (ATCC) (Manassas, Va.) and the NRRL Culture Collection (Agricultural Research Service, U.S. Department of Agriculture, Peoria, Ill.). The ATCC alone lists six strains of Mhyo for sale. In view of the widespread dissemination of the disease, strains may also be obtained by recovering Mhyo from lung secretions or tissue from sick animals and inoculating suitable culture medium.

Figure 1:
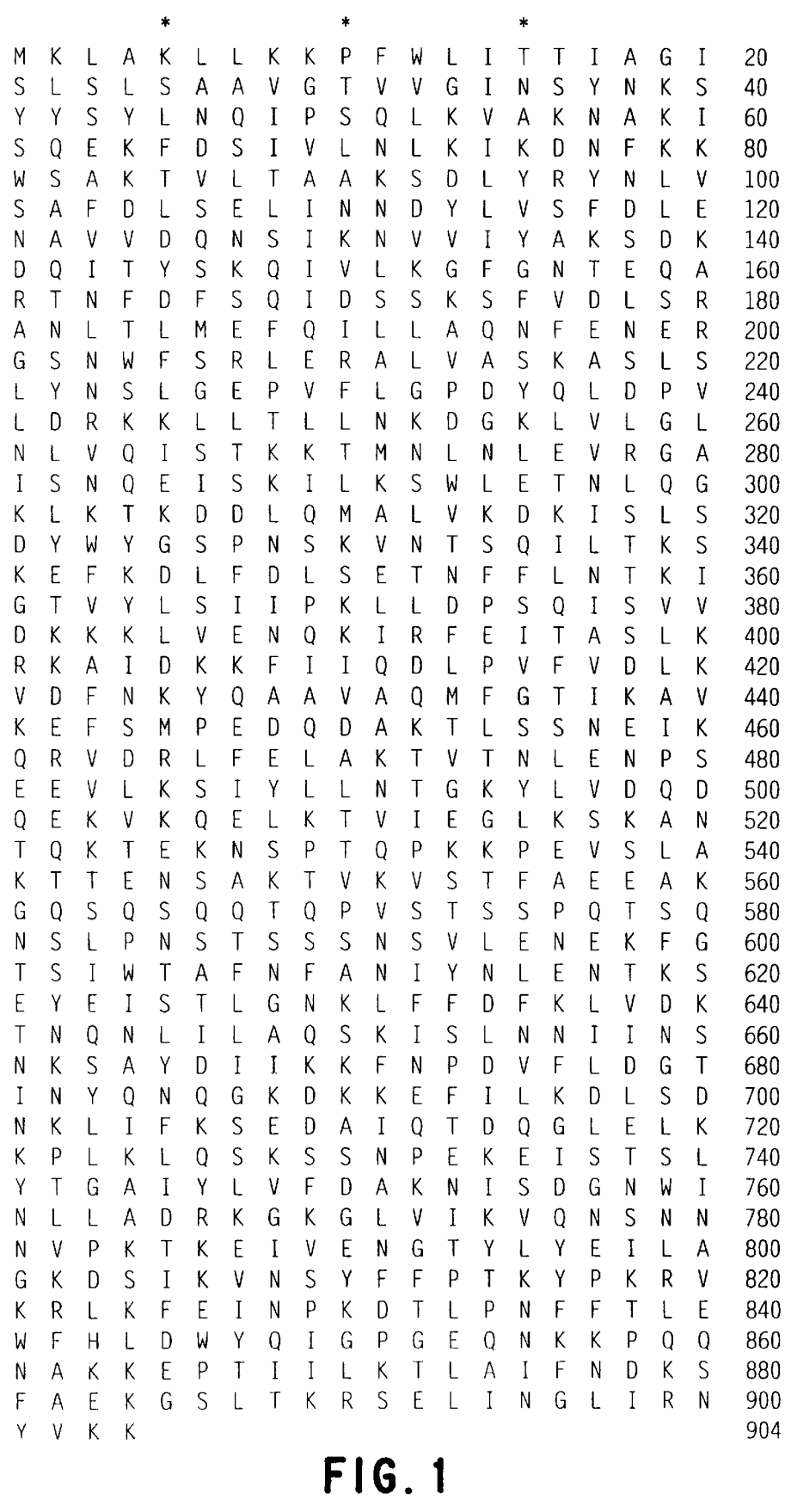

Referring now to the drawings, the amino acid sequence of Mhyo P102 is shown in FIG. 1. As can be seen, P102 comprises 904 amino acids, the distribution of which is detailed in Table 2, below. P102 lacks cysteine, and has

TABLE 2

Amino Acid Composition of The Translated P102 Sequence

| Amino Acid | Number[a] | Percentage[b] | Amino Acid | Number[a] | Percentage[b] |
|---|---|---|---|---|---|
| Non-polar: | | | Polar: | | |
| A | 45 | 4.98 | G | 33 | 3.65 |
| V | 52 | 5.75 | S | 86 | 9.51 |
| L | 103 | 11.39 | T | 54 | 5.97 |
| I | 62 | 6.86 | C | 0 | 0 |
| P | 28 | 3.10 | Y | 29 | 3.21 |
| M | 6 | 0.66 | N | 74 | 8.19 |
| F | 44 | 4.87 | Q | 47 | 5.20 |
| W | 9 | 1.00 | Basic: | | |
| Acidic: | | | K | 114 | 12.61 |
| D | 50 | 5.53 | R | 17 | 1.88 |
| E | 50 | 5.53 | H | 1 | 0.11 |

[a]Total number of individual aa.
[b]Percentage of each aa.

an isoelectric point (pI) of 9.28. The protein was designated as "P102" due to its 102.3 kiloDalton weight. It is believed that P102 may be a membrane-spanning protein, due to the presence of a putative 25 amino acid membrane-spanning domain at the N-terminus of the protein (aa 10–34). While not wishing to be bound by theory, the remainder of the protein sequence is currently believed to form one or more α-helices because of the high percentage (~64%) of α-helix forming amino acids present therein.

The proteins or polypeptides of the present invention have an amino acid sequence as shown in FIG. 1, or a fragment or mutant of said sequence capable of eliciting an antibody or other immune response which recognizes an epitope of the amino acid sequence depicted in FIG. 1. Mutations at either the amino acid or encoding DNA level may be useful in improving the yield of the proteins, their immunogenicity or antigenicity, or their compatibility with various purification schemes, adjuvants and modes of administration. Such fragments and mutations, synthetic or recombinant, are characterized by one or more of the antigenic sites of native Mhyo P102.

The proteins or polypeptides of the present invention may be purified or isolated proteins or polypeptides extracted from Mhyo cells, or may be recombinant proteins or polypeptides produced in hosts transformed by DNA sequences coding for those recombinant proteins or polypeptides. It should of course be understood that these proteins or polypeptides may include residues that are not related to Mhyo. For example, the recombinant proteins or polypeptides of this invention may be fusion proteins containing a protein portion derived from an expression vector or other source and a protein portion derived from Mhyo. These recombinant polypeptides and fusions of them may also include a starting methionine. All that is required is that the final polypeptides display the antigenicity of native Mhyo P102.

The recombinant DNA sequence encoding the P102 of the present invention, which comprises 2712 base pairs, is shown in FIG. 2. The sequence depicted is of the non-template strand, with the 5' end on the left and the 3' end on the right, so that mRNA produced from the complementary template strand will have a sequence identical to that shown in FIG. 2 except for the substitution of uracil (U) for thymine (T). The start codon (ATG) and stop codon (TAA) are underlined. Approximately 24 base pairs upstream of the start codon, including a putative Shine Dalgarno sequence (GGAGGT) 10 base pairs upstream of the start codon, and 21 base pairs downstream of the stop codon are also shown. The P102 sequence has no significant match to any known sequence, including other bacterial adhesin genes.

The present invention concerns any DNA sequence coding for a protein which is capable of eliciting an antibody or other immune response (e.g., T-cell response of the immune system) which recognizes an epitope of the amino acid sequence depicted in FIG. 1, including less than the full DNA sequence and mutants thereof. Hence the DNA sequence of the present invention may encode proteins or polypeptides which may be the full length antigen, antigen fragment, antigen derivative or a fusion product of such antigen, antigen fragment or antigen derivative with another protein.

Recombinant DNA molecules that are useful in preparing the aforementioned proteins and polypeptides are also provided. Preferred recombinant DNA molecules are characterized by a DNA sequence selected from the sequence shown in FIG. 2, cloning or expression vectors containing a sequence encoding a recombinant protein or polypeptide of the present invention, as described above, DNA sequences that hybridize to any of those DNA sequences and that code for Mhyo P102, DNA sequences that code for an antigen of Mhyo coded by any of the foregoing DNA sequences, and DNA sequences which are degenerate as a result of the genetic code to the aforementioned DNA sequences and which code for an antigen of Mhyo.

The appropriate DNA sequence may be inserted into any of a wide variety of expression vectors by a variety of procedures, generally through use of an appropriate restriction endonuclease site. Suitable vectors include, for example, vectors consisting of segments of chromosomal, non-chromosomal and synthetic DNA sequences, such as various known derivatives of SV40, known bacterial plasmids, e.g., plasmids from *E. coli* including col E1, pCR1, pBR322, pMB9 and their derivatives, wider host range plasmids, e.g., RP4, phage DNAs, e.g., the numerous derivatives of phage λ, e.g., NM 989, and other DNA phages such as M13 or filamentous single stranded DNA phages, yeast plasmids such as the 2$\mu$ plasmid or derivatives thereof, viral DNA such as baculovirus, vaccinia, adenovirus, fowl pox virus, or pseudorabies, and vectors derived from combinations of plasmids and phage DNAs, such as plasmids which have been modified to employ phage DNA or other expression control sequences.

Within each specific cloning or expression vehicle, various sites may be selected for insertion of the DNA sequences of this invention. These sites are usually designated by the restriction endonuclease which cuts them and there are various known methods for inserting DNA sequences into these sites to form recombinant DNA molecules. These include, for example, dG-dC or dA-dT tailing, direct ligation, synthetic linkers, exonuclease and polymerase-linked repair reactions followed by ligation, or extension of the DNA strand with DNA polymerase and an appropriate single-stranded template followed by ligation. It is, of course, to be understood that a cloning or expression vehicle useful in this invention need not have a restriction endonuclease site for insertion of the chosen DNA fragment, and that insertion may occur by alternative means.

For expression of the DNA sequences of this invention, these DNA sequences are operatively linked to one or more expression control sequences in the expression vector. Such operative linking, which may be effected before or after the chosen DNA sequence is inserted into a cloning vehicle, enables the expression control sequences to control and promote the expression of the inserted DNA sequence.

Any of a wide variety of expression control sequences—sequences that control the expression of a DNA sequence when operatively linked to it—may be used in these vectors to express the DNA sequences of this invention. Such useful expression control sequences include, for example, the early and late promoters of SV40, the lac or trp systems, the TAC or TRC system, the major operator and promoter regions of phage λ, the control regions of fd coat protein, the promoter for 3-phosphoglycerate kinase or other glycolytic enzymes, the promoters of acid phosphatase, e.g., Pho5, the promoters of the yeast α-mating factors, and other sequences known to control the expression of genes in prokaryotic or eukaryotic cells or their viruses, and various combinations thereof. The expression vector also includes a non-coding sequence for a ribosome binding site for translation initiation and a transcription terminator. The vector may also include appropriate sequences for amplifying expression. In mammalian cells, it is additionally possible to amplify the expression units by linking the gene to that coding for dehydrofolate reductase and applying a selection to host Chinese hamster ovary cells.

The vector or expression vehicle, and in particular the sites chosen therein for insertion of the selected DNA fragment and the expression control sequence employed in this invention are determined by a variety of factors, e.g., number of sites susceptible to a particular restriction enzyme, size of the protein to be expressed, expression characteristics such as the location of start and stop codons relative to the vector sequences, and other factors recognized by those of skill in the art. The choice of a vector, expression control sequence, and insertion site is determined by a balance of these factors, not all selections being equally effective for a given case.

In the preferred embodiments of this invention, various clones may be used, including those shown in FIGS. 3 through 5. FIG. 3 depicts a restriction map of various overlapping clones of the P97 operon, which includes the genes for Mhyo proteins P97 and P102. These clones were obtained by DNA hybridization with a cloned fragment from pISM1161. The position of the P97 structural gene, its direction of transcription (arrow), and the region of DNA sequence analysis (dark bar) are shown. Sites are given in kilobases. Restriction enzymes are abbreviated as follows: A, AccI; B, BamHI; Bg, BglII; C, ClaI; E, EcoRI; EV, EcoRV; H, HindIII; Hn, HincII; N, NciI; S, SalI.

FIG. 4 illustrates a restriction map of the P102-related clones of the present invention. The physical map of the P97 contig with the P97 and P102 gene boundaries is shown as a reference, and the direction of transcription is left to right. The homologies between the DNA sequences of clones pISM1232–34 and pISM2166 and the P97 operon sequence are indicated as shaded or hatched regions, with light gray indicating high (>95%) P102 homology, black indicating reduced (<75%) to no P102 homology, dark gray indicating no P97 homology, and hatched regions indicating regions for which no DNA sequence information was available. The positions of plasmids pISM1165, pISM1168, pISM1169, pISM1170, and pISM1174 relative to pISM1232 and pISM1233 are shown. Restriction patterns are given for each clone or group of clones, and size is given in kilobases.

Figure 5B:
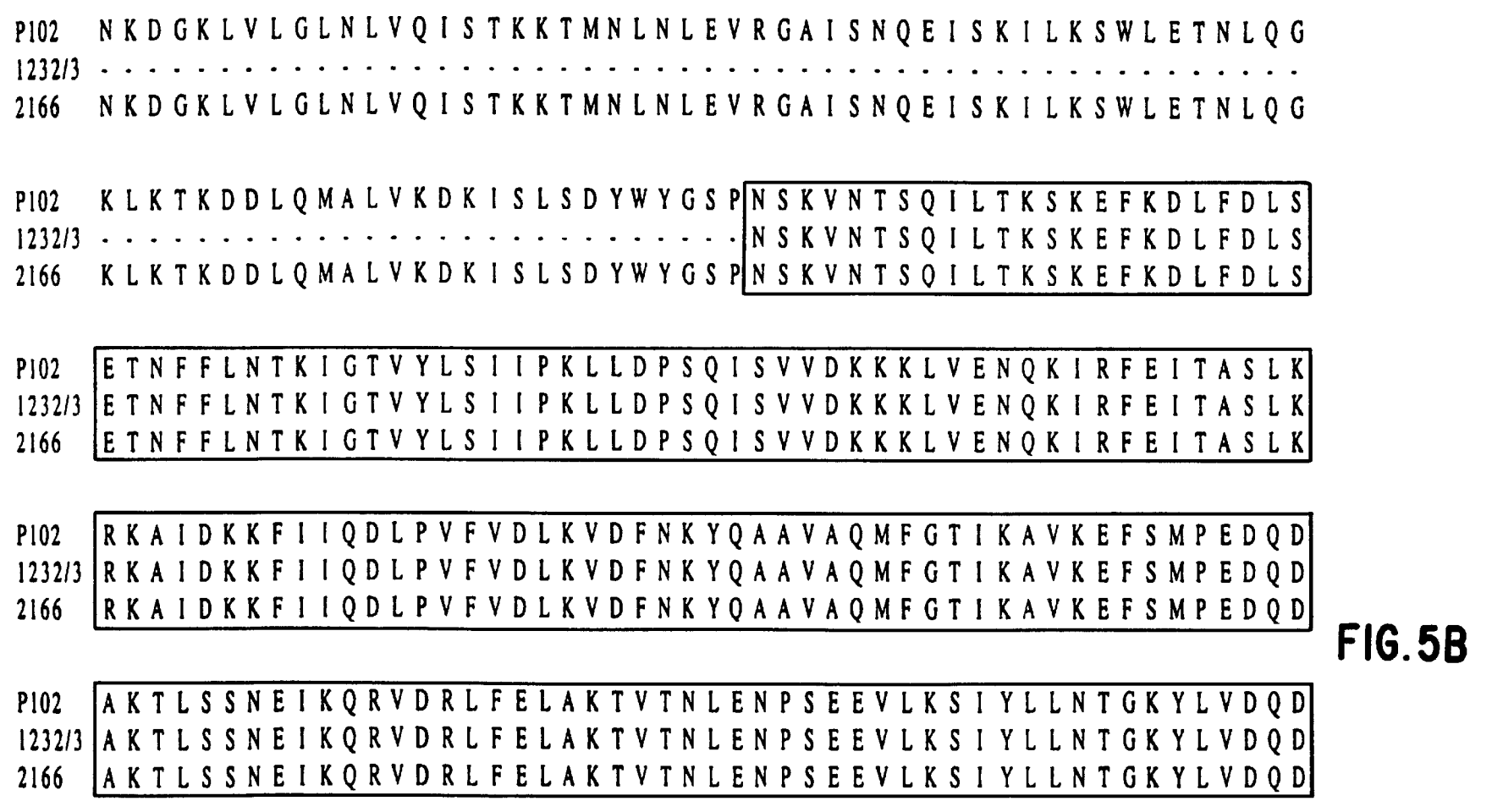

The alignment of the translated amino acid sequences of the P102 clones pISM2166, pISM1232, pISM1233, and pISM1234 with native P102 is shown in FIG. 5. Alignment of the P102 amino acid sequences was done using Clustal W alignment in MacVector™ software version 6.0.1 (Oxford Molecular Group, Campbell, Calif.). Boxed areas indicate identity or similarity in the sequence. pISM1232/3 indicates alignment for both pISM1232 and pISM1233. Sequences for pISM1232 are shown at the beginning of the alignment and sequences for pISM1233 are shown at the end of the alignment.

The recombinant DNA molecule containing the desired gene operatively linked to an expression control sequence may then be employed to transform a wide variety of appropriate hosts so as to permit such hosts (transformants) to express the gene, or fragment thereof, and to produce the polypeptide, or portion thereof, for which the hybrid DNA codes. The recombinant DNA molecule may also be employed to transform a host so as to permit that host on replication to produced additional recombinant DNA molecules as a source of Mhyo genes and fragments thereof.

A wide variety of hosts are also useful in producing the antigens and DNA sequences of this invention. These hosts include, for example, bacteria such as *E. coli*, Bacillus and Streptomyces, fungi such as yeasts, and animal or plant cells in tissue culture. The selection of an appropriate host for either of these uses is controlled by a number of factors. These include, for example, compatibility with the chosen vector, toxicity of the co-products, ease of recovery of the desired polypeptide, expression characteristics, biosafety and costs. No absolute choice of host may be made for a particular recombinant DNA molecule or polypeptide from any of these factors alone. Instead, a balance of these factors must be struck with the realization that not all hosts may be equally effective for expression of a particular recombinant DNA molecule.

It is also understood that the DNA sequences that are inserted at the selected site of a cloning or expression vehicle may include nucleotides which are not part of the actual gene coding for the desired polypeptide or may include only a fragment of the entire gene for that protein. It is only required that whatever DNA sequence is employed, the transformed host produces a polypeptide having the antigenicity of native Mhyo P102.

For example, the DNA sequences of this invention may be fused in the same reading frame in an expression vector of this invention to a portion of a DNA sequence coding for at least one eukaryotic or prokaryotic carrier protein or a DNA sequence coding for at least one eukaryotic or prokaryotic signal sequence, or combinations thereof. Such constructions may aid in expression of the desired DNA sequence, improve purification or permit secretion, and preferably maturation, of the desired polypeptide from the host cell. The DNA sequence may alternatively include an ATG start codon, alone or together with other codons, fused directly to the sequence encoding the first amino acid of a desired polypeptide. Such constructions enable the production of, for example, a methionyl or other peptidyl polypeptide that is part of this invention. This N-terminal methionine or peptide may then be cleaved intra- or extra-cellulary by a variety of known processes or the polypeptide used together with the methionine or other fusion attached to it in the compositions and methods of this invention.

The appropriate DNA sequence present in the vector when introduced into a host may express part or only a portion of the protein which is encoded, it being sufficient that the expressed protein be capable of eliciting an antibody or other immune response which recognizes an epitope of the amino acid sequence depicted in FIG. 1. For example, in employing *E. coli* as a host organism, the UGA codon is a stop codon so that the expressed protein may only be a fragment of the antigen encoded into the vector and for this reason it is generally preferred that all of the UGA codons in the appropriate DNA sequence be converted into non-stop codons. Another way around the problem in a host that recognizes UGA as a stop codon is to include an additional DNA sequence which encodes a t-RNA which translates the UGA codon within a protein coding sequence as tryptophan in the transformed organism.

The protein expressed by the host transformed by the vector may be harvested by methods which will occur to those skilled in the art, and used in a vaccine for protection of a non-human animal such as swine, cattle, etc. against enzootic pneumonia caused by Mhyo. The protein is used in an amount effective to provide protection against enzootic pneumonia caused by Mhyo and may be used in combination with an suitable physiologically acceptable carrier, as is described below in more detail.

In a preferred embodiment of the invention, the gene sequence for P102 was cloned into the expression vector pTrcHis Xpress available from Invitrogen Corp. (Carlsbad, Calif.). An *E. coli* host was transformed with the vector, and P102 protein was produced at high levels. The pTrcHis Xpress vector produced a fusion protein comprising P102 fused to a short leader peptide with six histidine residues in tandem. The cells were then lysed, and P102 was purified by running the crude cell lysate through a metal chelate column, such as a ProBond column (Invitrogen, Carlsbad, Calif.).

The recombinant proteins and polypeptides of the present invention may also be used as antigens for diagnostic purposes to determine whether or not a biological test sample contains Mhyo antigens or antibodies to these antigens. Such an assay for Mhyo infection in an animal typically comprises incubating an antibody-containing biological sample from an animal suspected of having such a condition in the presence of a detectably labeled recombinant protein of the present invention, and detecting binding.

Thus, in this aspect of the invention, the recombinant proteins may be associated with a solid phase support, e.g., a microtiter plate, which is capable of immobilizing cells, cell particles or soluble proteins. The support may then be washed with suitable buffers followed by treatment with the sample containing antibody. The solid phase support may then be washed with the buffer a second time to remove unbound antibody. Labeled recombinant protein is added and the support is washed a third time to remove unbound labeled antigen. The amount of bound label on said solid support may then be detected by conventional means.

By “solid phase support” is intended any support capable of binding antigen or antibodies. Well-known supports, or carriers, include glass, polystyrene, polypropylene, polyethylene, dextran, nylon, amylases, natural and modified celluloses (especially nitrocellulose), polyacrylamides, agarose, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads.

One of the ways in which the Mhyo specific antibody can be detectably labeled is by linking the same to an enzyme and using it in an enzyme immunoassay (EIA), or enzyme-linked immunosorbent assay (ELISA). This enzyme, in turn, when later exposed to its substrate, will react with the substrate in such a manner as to produce a chemical moiety which can be detected, for example, by spectrophotometric, fluorometric or by visual means. Enzymes which can be used to detectably label the Mhyo specific antibody include, but are not limited to, horseradish peroxidase, malate dehydrogenase, staphylococcal nuclease, delta-V-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoa/nylase and acetylcholinesterase.

Detection may be accomplished using any of a variety of immunoassays. For example, by radioactively labeling the recombinant protein, it is possible to detect antibody binding through the use of a radioimmunoassay (RIA). The radioactive isotope can be detected by such means as the use of a gamma counter or a scintillation counter or by autoradiography. Isotopes which are particularly useful for the purpose of the present invention are $^3$H, $^{125}$I, $^{131}$I, $^{35}$S, and $^{14}$C, preferably $^{125}$I.

It is also possible to label the recombinant protein with a fluorescent compound. When the fluorescently labeled protein is exposed to light of the proper wavelength, its presence can then be detected due to fluorescence. Among the most commonly used fluorescent labeling compounds are fluorescein isothiocyanate, rhodamine, phycoerytherin, phycocyanin, allophycocyanin, o-phthaldehyde and fluorescamine. The protein can also be detectably labeled using fluorescence emitting metals such as $^{152}$Eu, or others of the lanthanide series. These metals can be attached to the protein using such metal chelating groups as diethylenetriaminepentaacetic acid (DTPA) or ethylenediamine-tetraacetic acid (EDTA).

The protein also can be detectably labeled by coupling it to a chemiluminescent or bioluminescent compound. The presence of the chemiluminescent-tagged protein is then determined by detecting the presence of luminescence that arises during the course of a chemical reaction. Bioluminescence is a type of chemiluminescence found in biological systems in which a catalytic protein increases the efficiency of the chemiluminescent reaction. Examples of particularly useful chemiluminescent labeling compounds are luminol, isoluminol, theromatic acridinium ester, imidazole, acridinium salt and oxalate ester. Important bioluminescent compounds for purposes of labeling are luciferin, luciferase and aequorin.

Detection of the label may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

The detection of foci of detectably labeled antibodies is indicative of a disease or dysfunctional state and may be used to measure Mhyo in a sample. The absence of such antibodies or other immune response indicates that the animal has been neither vaccinated nor infected. For the purposes of the present invention, the bacteria which is detected by this assay may be present in a biological sample. Any sample containing it can be used, however, one of the benefits of the present diagnostic invention is that invasive tissue removal may be avoided. Therefore, preferably, the sample is a biological solution such as, for example, nasal, throat or lung fluid, but the invention is not limited to assays using these samples.

In situ detection may be accomplished by removing a histological specimen from an animal, and providing the combination of labeled antibodies of the present invention to such a specimen. The antibody (or fragment) is preferably provided by applying or by overlaying the labeled antibody (or fragment) to a biological sample. Through the use of such a procedure, it is possible to determine not only the presence of Mhyo but also the distribution of it in the examined tissue. Using the present invention, those of ordinary skill will readily perceive that any of a wide variety of histological methods (such as staining procedures) can be modified in order to achieve such in situ detection.

Alternatively, a fluid sample may be tested for the presence of a gene for Mhyo P102 by reaction with a recombinant or synthetic DNA sequence contained within the sequence shown in FIG. 2 or any RNA sequence equivalent to said DNA sequence. The absence of the gene indicates that the animal has been neither vaccinated nor infected. This test involves methods of synthesis, amplification or hybridization of nucleic acid sequences which are known to those skilled in the art.

The present invention also contemplates a vaccine, comprising the recombinant proteins and polypeptides of the present invention, or DNA sequences encoding these proteins and polypeptides, for immunizing or protecting non-human animals, preferably swine, against Mhyo infections, particularly enzootic pneumonia. The terms "protecting" or "protection" when used with respect to the vaccine for enzootic pneumonia described herein means that the vaccine prevents enzootic pneumonia caused by Mhyo and/or reduces the severity of the disease.

A vaccine based on the DNA sequences of the present invention may be made by removing UGA codons and introducing the chosen sequence into a suitable vector. The vaccine may then be administered by suitable methods such as particle bombardment, microinjection, electroporation, calcium phosphate transfection, liposomal transfection, and viral transfection. DNA vaccines and methods of their administration are known in the art, and are described in U.S. Pat. Nos. 5,836,905; 5,703,055; 5,589,466; and 5,580, 859, which are herein incorporated by reference.

The vaccine is employed in conjunction with a carrier, which may be any of a wide variety of carriers. Representative carriers include sterile water, saline, buffered solutions, mineral oil, alum, synthetic polymers, etc. Additional agents to improve suspendability and dispersion in solution may also be used. The selection of a suitable carrier is dependent upon the manner in which the vaccine is to be administered. The vaccine is generally employed in non-human animals which are susceptible to enzootic pneumonia, and in particular swine.

The vaccine may be administered by any suitable method, such as intramuscular, subcutaneous, intraperitoneal or intravenous injection. Alternatively, the vaccine may be administered intranasally or orally, such as by mixing the active components with feed or water, providing a tablet form, etc. Methods such as particle bombardment, microinjection, electroporation, calcium phosphate transfection, liposomal transfection, and viral transfection are particularly suitable for administering a DNA sequence vaccine. Other means for administering the vaccine will be apparent to those skilled in the art from the teachings herein; accordingly, the scope of the invention is not limited to a particular delivery form. The vaccine may also include active components or adjuvants (e.g., Freund's incomplete adjuvant) in addition to the antigen(s) or fragments hereinabove described.

Adjuvants may be used to enhance the immunogenicity of an antigen. The mechanism of how adjuvants operate is not entirely known. Some are believed to enhance the immune response by slowly releasing the antigen while other adjuvants are believed to function synergistically. Among the adjuvants which may be used are oil and water emulsions, complete Freund's adjuvant, incomplete Freund's adjuvant, *Corynebacterium parvum*, Hemophilus, *Mycobacterium butyricum*, aluminum hydroxide, dextran sulfate, iron oxide, sodium alginate, Bacto-Adjuvant, certain synthetic polymers such as poly amino acids and co-polymers of amino acids, saponin, iota carrageenan, Regressin™, Avridine™, *Mannite monooleate*, paraffin oil, and muramyl dipeptide.

Application of the teachings of the present invention to a specific problem or environment is within the capabilities of one having ordinary skill in the art in light of the teachings contained herein. Examples of the products and processes of the present invention appear in the following examples.

EXAMPLE 1

Library Construction and Screening

A Mhyo chromosomal DNA genomic library was constructed with Tsp5091-digested chromosomal DNA cloned into EcoRI λ ZAP II as described previously in Minion, F. C., VanDyk, C. and Smiley, B. K., "Use of an *Escherichia coli* enhanced opal suppressor strain to screen a *Mycoplasma hyopneumoniae* library", 131 *FEMS Microbiol. Letters* 81–85 (1995), which is herein incorporated by reference. The library was grown on *E. coli* strain LE392 using the technique described in Hanahan, D., "Studies on transformation of *Escherichia coli* with plasmids", 166 *J. Mol. Biol.* 557–80 (1983), and screened by DNA hybridization using the method of Sambrook, J., Fritsch, E. F. and Maniatis, T., Molecular cloning: A Laboratory Manual, Cold Spring Harbor Laboratory, Cold Spring Harbor, N.Y. (1989), and with swine convalescent antisera as described in Minion et al.

Figure 6:
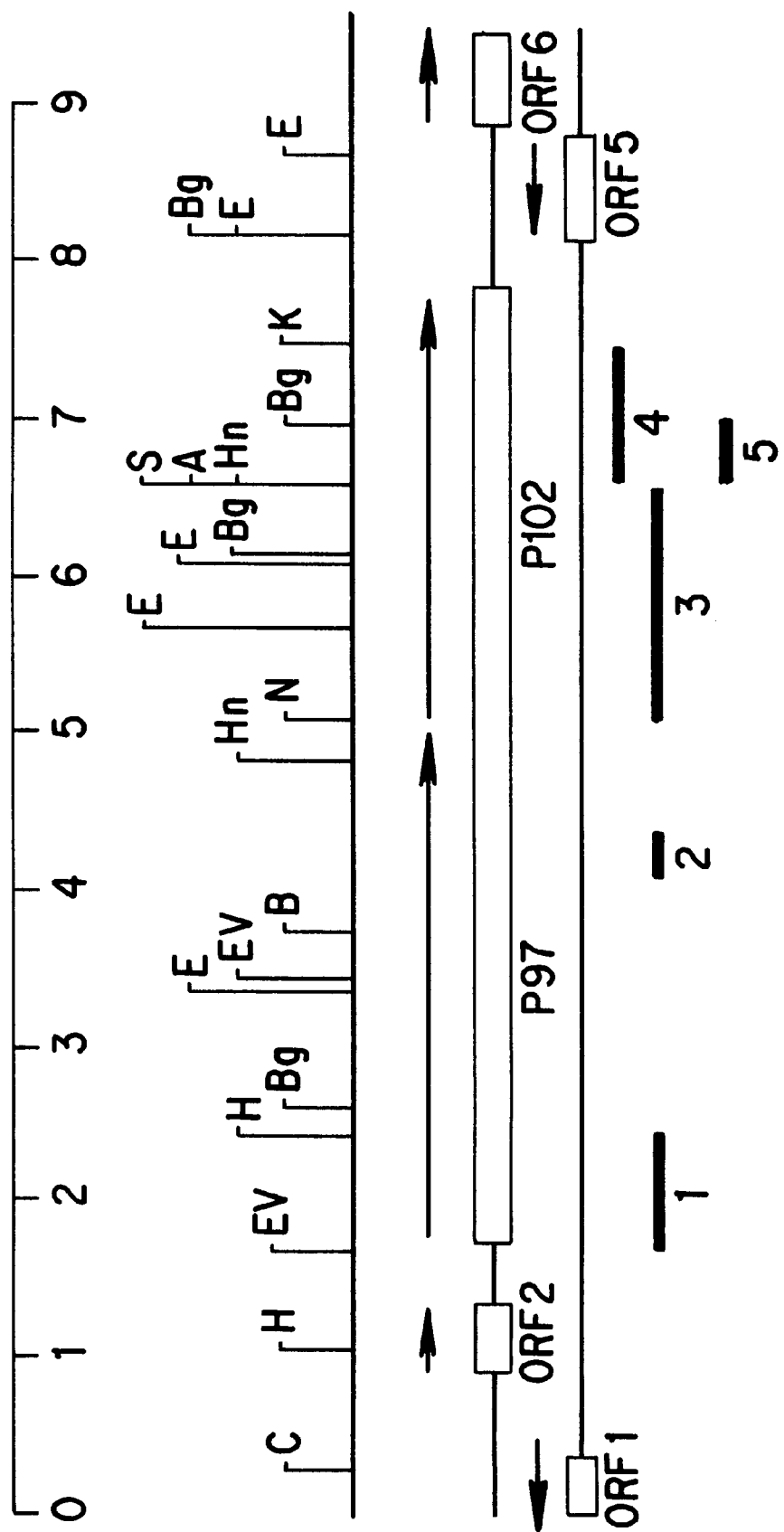
FIG. 6 depicts the open reading frames of the P97 contig, and the probes used to screen the genomic library.

FIG. 6 illustrates the open reading frames of the P97 contig, and the probes used to screen the genomic library. Boxes indicate ORFs with their designations given below. Shaded boxes indicate transcription from left to right; white boxes indicate transcription from right to left. Probes 1–4 used for hybridization analysis, and probe 5 used in screening the genomic library are shown below the figure. Hybridization was carried out overnight with $^{32}$P radiolabeled probes at 65° C. One hybridization probe was the 3.3-kb cloned fragment from pISM1161 containing the N-terminus of P97 as well as upstream sequences depicted in FIG. 3. A second probe, probe 5, was a cloned 400-bp fragment of DNA located in the P102 structural gene, as shown in FIG. 6.

The library was also screened with Mhyo-infected swine convalescent sera as described previously in Minion et al. Convalescent sera was obtained by the following process. Inoculum was made by removing swine lungs infected with Mhyo from an animal, homogenizing them, and then freezing aliquots. Next, an aliquot of inoculum was diluted 1:10 in steryl phosphate-buffered saline and 10 mL was instilled intertracheally in swine. Blood was drawn to obtain sera after 28 days, or after 56–73 days. Plasmids containing cloned Mhyo chromosomal DNA fragments were excised in vivo from the corresponding purified recombinant λ ZAP II phage with ExAssist™ helper phage (Stratagene, La Jolla, Calif.) and introduced into the *E. coli* SOLR™ [e14-(mcrA) Δ(mcrCB-hsdSMR-mr$^R$)171 sbcC recB recJ uvrC umuC::Tn5(Kn$^R$) lac gyrA96 relA1 thi-1 endA1 λ$^R$ (F$^1$ proAB lacI$^q$Z M15) Su$^-$] according to the manufacturer's instructions (Stratagene, La Jolla, Calif.).

EXAMPLE 2

DNA Sequencing and Sequence Analysis

Tn1000-facilitated DNA sequencing was performed on plasmids pISM1210, pISM1217 and PISM2166 as described by Strathmann, M., Hamilton, B. A., Mayeda, C. A., Simon, M. I., Meyerowitz, E. M. and Palazzolo, M. J., "Transposon-facilitated DNA sequencing", 88 *Proc. Nat'l Acad. Sci. USA* 1247–50 (1991). Matings were performed with *E. coli* strains DPWC(F$^+$), as described in Strathmann et al. and BW26 (Kn$^R$ recipient). The inserts were mapped by restriction digests using SalI, EcoRV and BamHI restriction enzymes, and a series of Tn1000 inserts were chosen to use as template DNAs for sequencing reactions based upon their location and their usefulness in adding to the DNA sequence information upstream and downstream of the P97 sequence. DNA sequencing was then performed, as described in Strathmann et al., using the T7 and T3 vector-specific primer sites and Tn1000 end-specific primers 186 (SEQ ID NO:6) (5'-ATATAAACAACGAATTATCTCC-3') and 188 (SEQ ID NO:7) (5'-TAAGTTATACCATAAACG-3') in cycle sequencing reactions. All sequences were obtained using an automated Model 373A Fluorescent DNA sequencer (Perkin-Elmer Applied Biosystems, Inc., Foster City, Calif.). DNA sequence analysis was performed with MacVector™ software version 6.0.1 (Oxford Molecular Group, Campbell, Calif.). Translation was performed with a mycoplasma translation table. DNA and translated protein sequence homology searches were accomplished by BLASTN and BLASTP analyses, respectively.

EXAMPLE 3

Hybridization Analysis

Hybridization analysis was performed on Mhyo chromosomal DNA digested with HindIII, HincII, EcoRV, EcoRI, and BglII. The digested DNAs were resolved on 0.7% agarose gels and blotted on to a nylon membrane. Several P97 operon-specific probes, shown in FIGS. 3 and 6, were used in the analysis, including a 758-bp EcoRV-HindIII fragment of P97 obtained from pISM1213 (probe 1), a PCR product containing the R1 repeat region of P97 that contains the major antigenic and the cilium binding epitopes (probe 2), and the NciI-HincII (probe 3) and HincII-KpnI (probe 4) fragments from pISM2139.

Primers TH120 (SEQ ID NO:8) (5'-AAGGTAAAAGAGAAGAAGTAG) and TH121 (SEQ ID NO:9) (5'-TTGTAAGTGAAAAGCCAGTAT) were used in a PCR reaction mixture containing 2 mM MgCl$_2$, 25 pmol of each primer, 1–50 ng template DNA, 1.25 units of Taq DNA polymerase in 50 µl of 1X manufacturer's reaction buffer to generate probe 2. The PCR conditions were as follows: the DNA was denatured at 94° C. for 5 min, followed by 35 cycles (94° C. denaturation for 1 min, 58° C. annealing for 1.5 min and 72° C. extension for 1 min) and a final 5-min 72° C. extension step.

Figure 7:
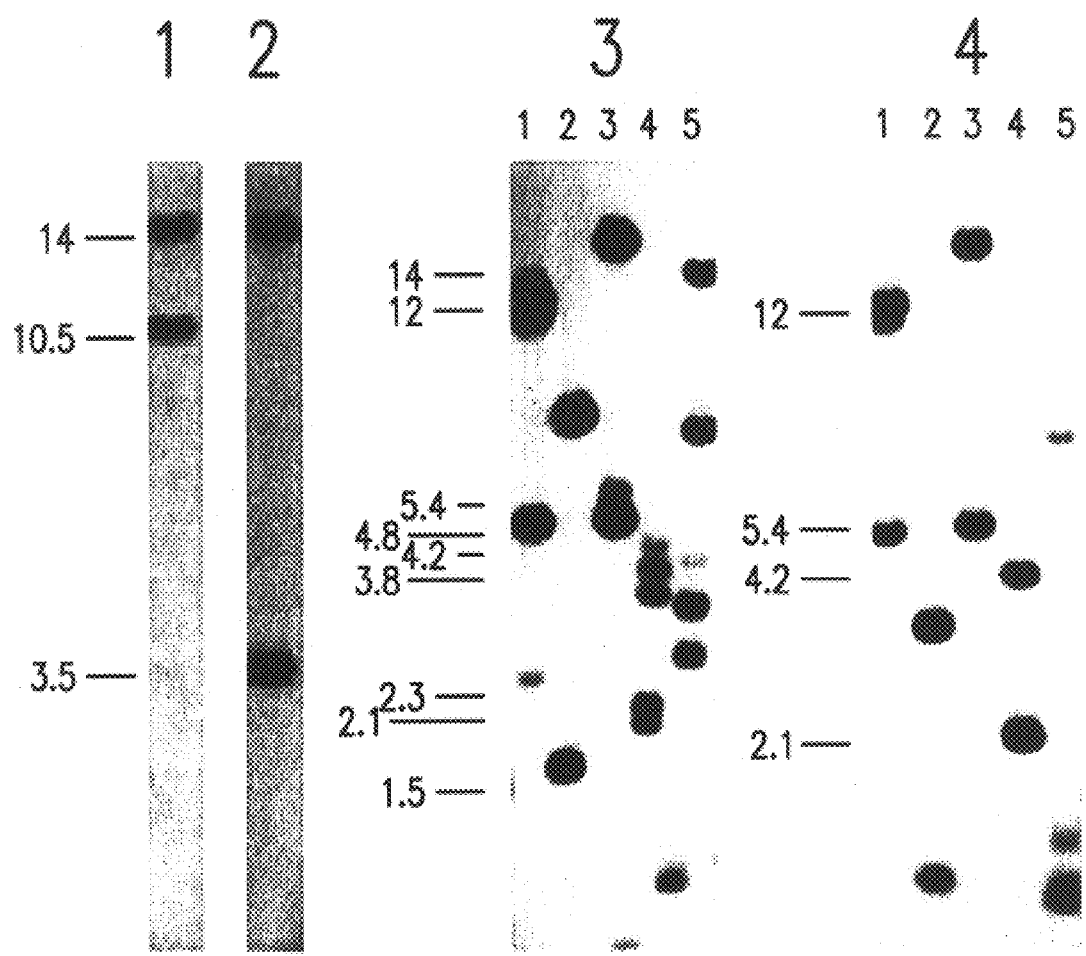
FIG. 7 depicts the results of a hybridization analysis of Mhyo DNA with the probes of FIG. 6.

FIG. 7 depicts the results of a hybridization analysis of Mhyo DNA with the probes of FIG. 6. Each panel represents hybridization with a single probe as indicated at the top of the panel. For probes 1 and 2, the chromosomal DNA was digested with BglII. Restriction enzyme digested chromosomal DNAs for probes 3 and 4 were HindIII (lane 1), HincII (lane 2), EcoRV (lane 3), EcoRI (lane 4), and BglII (lane 5). Lane 6 contained 6 ng of control plasmid DNA digested with the enzymes used to isolate the probe. The autoradiographs were digitized using a Cohu model 4900 high-performance CCD camera (Cohu Inc., San Diego, Calif.) and a Macintosh IIci equipped with a Scion Corporation (Frederick, Md.) video board. The size of each band was determined using (GelReader software (NCSA, Urbana-Champaign, Ill.), and the sizes are indicated in kilobases. TIFF files were cropped with and assembled in Adobe Photoshop and labeled in Aldus FreeHand (Adobe Systems Inc., San Jose, Calif.).

EXAMPLE 4

Cloning and Analysis of P102 Gene Copies

Additional clones of P102 were obtained by cloning agarose gel purified 3.8-, 4.2- and 4.8-kb EcoRI fragments of Mhyo chromosomal DNA into EcoRI-digested pBluescript II pSK⁻ (Stratagene, La Jolla, Calif.). Recombinant clones were then screened by colony blot for P102-specific clones using probe 3 (shown in FIG. 6). These resulting plasmids were restriction mapped and the ends of the cloned fragments sequenced. A sequencing primer (SEQ ID NO:10) (5'-GCGGCTGCTAAACTAAGACTA) was used to obtain additional sequence information of the 3' end of pISM1232 and pISM1234, which was aligned to the P97 contig sequence. An additional clone, pISM2166, which was obtained by screening the genomic library with swine convalescent antisera, was completely sequenced and was found to contain significant homology to P102.

EXAMPLE 5

Identification and Characterization of the P102 Structural Gene

All previous recombinant clones containing P97 sequences were identified using mAb F1B6, as described in Hsu, T., Artiushin, S. and Minion, F. C., "Cloning and analysis of P97, a respiratory cilium adhesin gene of *Mycoplasma hyopneumoniae*", 179 *J. Bacteriol.* 1317–23 (1997). To obtain additional clones containing the P97 structural gene and its surrounding sequences, we screened the genomic library by hybridization using a probe that contained the P97 5' end and sequences upstream of the translational start codon. An additional clone was identified with P102 sequences by screening the library with swine convalescent sera from Mhyo-infected pigs. The resulting clones were then subjected to DNA sequence and hybridization analyses.

Figure 4:
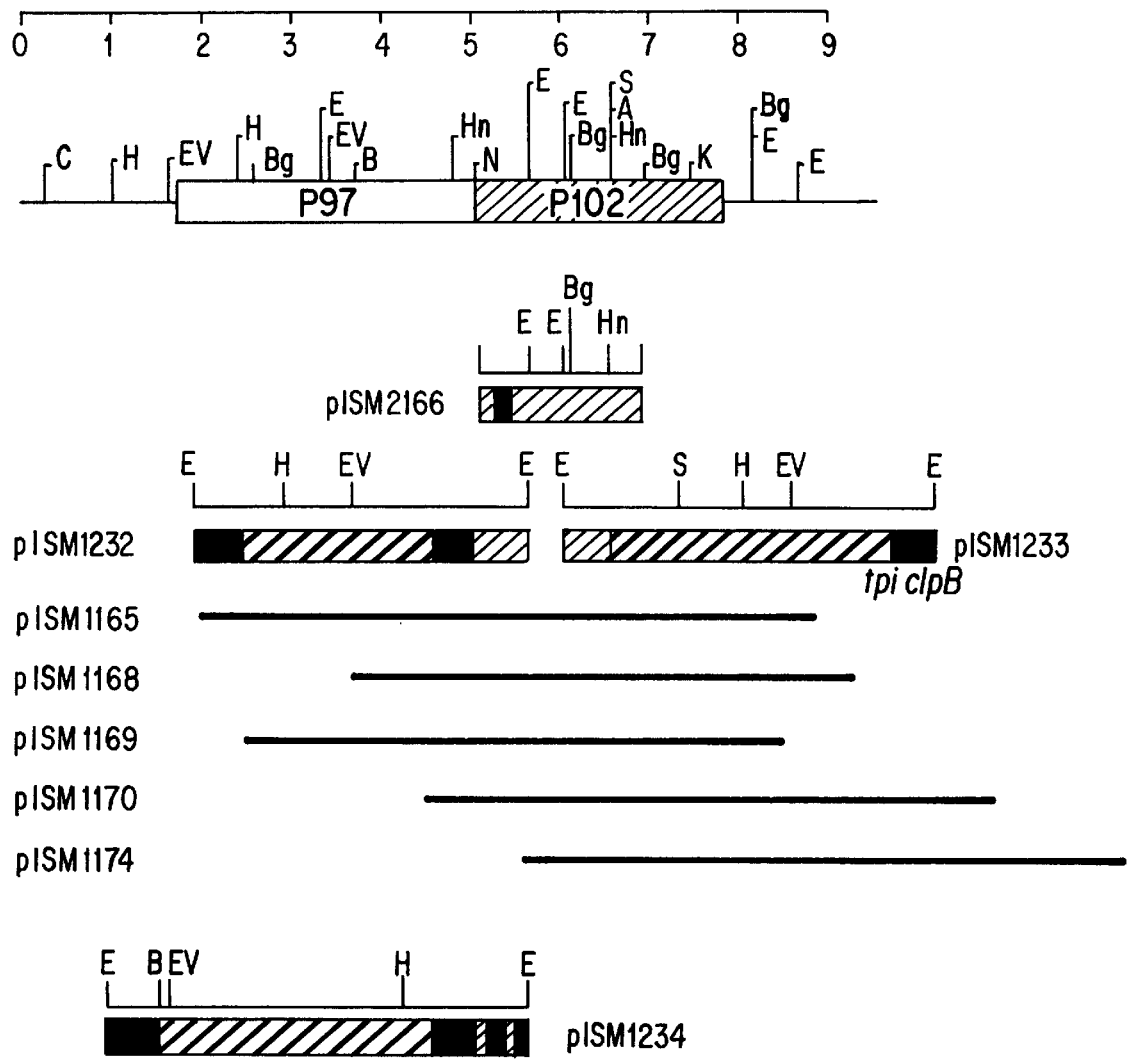
FIG. 4 depicts a restriction map of the P102 clones.

Screening of the genomic library with the 3.3-kb fragment from pISM1161 resulted in the identification of clones pISM1210, pISM1212–pISM1214, and pISM1217, as shown in FIG. 3. These plasmids, represented by the two largest plasmids pISM1210 and pISM1217, overlapped a 16-kb region (designated as the P97 contig) corresponding to the upstream and downstream regions of the P97 gene, respectively. Among the clones identified with probe 5 were pISM1165, pISM1168–pISM1170, and pISM1174 (FIG. 4).

A total of 9374 bp of DNA sequence were obtained, including the sequence for P97. FIG. 2 depicts the approximately 2750 bp sequence that includes the P102 gene. The complete sequence of the P97 operon has been published previously in Hsu, T. and Minion, F. C., "Molecular analysis of the P97 cilium adhesin operon of *Mycoplasma hyopneumoniae*", 214 *Gene* 13–23 (1998), and in Hsu et al. (Accession No. U50901). Computer analysis identified a total of six ORFs in this 9374-bp sequence (FIG. 6). P97 appeared to be the first gene of a two-gene operon, designated as the P97 operon, and depicted in FIGS. 4 and 6. The two genes are separated by 20 bp, which includes a putative Shine Dalgarno sequence (GGAGGT) 10 bp upstream of the ATG start codon of the second ORF. This ORF was 2712 bp in length with a coding capacity for a 102.3-kDa protein. This protein was designated as P102, had a calculated pI of 9.28, and lacked Cys (see Table 2 above).

The protein was highly hydrophilic with a putative 25-aa membrane-spanning domain at its N-terminus (aa 10–34). A search of the database for homology with P102 revealed no significant match to any known sequence, including other bacterial adhesin genes. The protein structural predictions for P102 indicate a high degree of α-helicity following a hydrophobic transmembrane sequence (data not shown).

To verify the hypothesis that additional copies of P102 were present in the Mhyo chromosome, the additional EcoRI chromosomal fragments recognized by P102-specific probes were cloned and analyzed. Plasmids pISM1232–pISM1234 representing the 3.8-, 4.2- and 4.8-kb fragments, respectively, were restriction-site-mapped. Partial sequencing of the ends of 3.8 and 4.2 kb cloned fragments suggested that these two clones are from a different chromosomal region to the original P102 copy. Alignment of the cloned fragments with the P97 contig is shown in FIG. 4. The DNA sequence of the 3' end of pISM1232 and the 5' end of pISM1233 aligned well with the P102 sequence and the intervening sequence between P97 and P102, but the homology ended abruptly at the 3' end of the P97 gene sequence (FIG. 4). The 5' end of pISM1232 showed no homology with the P97 gene or any other known sequence. The 3' end of pISM1233 had homology at the protein level with the *Corynebacterium glutamicum* heat-shock protein ClpB (62% identity and 84% similarity in a 98-aa region between aa 158 and 256 of the *C. glutamicum* sequence). Located upstream of the clpB sequence was the Mhyo triosephosphate isomerase gene tpi (Accession No. L33478). A series of overlapping clones (pISM1165, pISM1168–pISM1170, and pISM1174) with similar restriction maps to pISM1232 and pISM1233 was obtained from the genomic library using a 400-bp probe derived from P102 sequences. The alignment of these clones relative to pISM1232 and pISM1233 is shown in FIG. 4. No sequence information was obtained from these clones, but their restriction maps indicate that they are from the same chromosomal region as pISM1232 and pISM1233.

The DNA sequence information obtained from plasmid pISM1234 containing the 4.8-kb hybridizing fragment showed short stretches of DNA homology with P102 interspersed with non-homologous regions. Two stretches of 130 bp (82% homology with P102) and 177 bp (95% homology with P102) were identified, as shown in FIG. 5, explaining its weak reaction with the P102-specific probe 3. Since clones pISM1232–pISM1234 were not completely sequenced, it is possible that other homologies with P102 are present in the cloned fragments that have not been identified.

Clone pISM2166 represents an almost completely homologous copy of P102. The 1624-bp sequence shows divergence only in the 144–330 bp (48–110 aa) region, as can be seen in FIGS. 4 and 5. The restriction pattern of P102 is almost completely identical to that of the P97 operon sequence, except for the absence of SalI and AccI sites (FIG. 4). SalI is a rare cutting enzyme in Mhyo so the loss of this site in the copy of P102 is significant. It is our conclusion that pISM2166 represents a second copy of P102. Plasmids pISM1232 and pISM1233 also show a good alignment with P102 (FIG. 5), but their restriction patterns and the upstream sequences of pISM1232 show that these fragments are derived from a third chromosomal location. Plasmids pISM1232 and pISM1233 are probably from the same chromosomal location, because clones pISM1165, pISM1168–pISM1170 and pISM1174 overlapped the region with identical restriction patterns. Plasmid pISM1234 has only two short stretches of homology to P102 recognized by our limited sequence analysis. It is clear, however, that this fragment is derived from another chromosomal region.

EXAMPLE 6

Use of the P102 Protein in Detecting the Presence of *Mycoplasma Hyopneumoniae* Infection in Swine (Prospective Example)

The polypeptides displaying *Mycoplasma hyopneumoniae* antigenicity of this invention may be used in methods and kits designed to detect the presence of *Mycoplasma hyopneumoniae* infection in swine herds and therefore to recognize swine in a herd which have been infected by this virus, in order to permit early vaccination of the herd against the infection. For example, the antigens produced by hosts transformed by recombinant DNA molecules of this invention, or antibodies raised against them, can be used in RIA or ELISA for these purposes. In one type of radioimmunoassay, antibody against one or more of the antigens of this invention, raised in a laboratory animal (e.g., rabbits), is attached to a solid phase, for example, the inside of a test tube. Antigen is then added to the tube so as to bind with the antibody.

A sample of swine serum, taken from 1 of each 10 to 20 swine per herd, together with a known amount of antigen antibody labeled with a radioactive isotope, such as radioactive iodine, is then added to the tube coated with the antigen-antibody complex. Any antigen (a marker for Mhyo infection) antibody in the swine serum will compete with the labeled antibody for the free binding sites on antigen-antibody complex. Once the serum has been allowed to interact, the excess liquid is removed, the test tube washed, and the amount of radioactivity measured. A positive result, i.e., that the tested swine's serum contains Mhyo antibody, is indicated by a low radioactive count.

In one type of ELISA test, a microtiter plate is coated with one or more antigens of this invention and to this is added a sample of swine serum, again, from 1 in every 10 or 20 swine in a herd. After a period of incubation permitting interaction of any antibody present in the serum with the antigen, the plate is washed and a preparation of antigen antibodies, raised in a laboratory animal and linked to an enzyme label, is added, incubated to allow reaction to take place, and the plate is then rewashed. Thereafter, enzyme substrate is added to the microtiter plate and incubated for a period of time to allow the enzyme to work on the substrate, and adsorbance of the final preparation is measured. A large change in adsorbance indicates a positive result, i.e., the tested swine serum had antibodies to Mhyo and was infected with that bacteria.

EXAMPLE 7

Use of the Antigens and Sequences of This Invention in Vaccines against *Mycoplasma hyopneumoniae* Infections (Prospective Example)

Standard methods known to those skilled in the art may be used in preparing the vaccine of the present invention for administration to swine. For example, the polypeptide of choice may be dissolved in sterile saline solution. For long term storage, the polypeptide may be lyophilized and then reconstituted with sterile saline solution shortly before administration. Prior to lyophilization, preservatives and other standard additives such as those to provide bulk, e.g., glycine or sodium chloride, may be added. A compatible adjuvant may also be administered with the vaccine.

A vaccine in accordance with this invention can also be prepared using antibodies raised against the polypeptides of this invention in laboratory animals, such as rabbits. This "passive" vaccine can then be administered to swine to protect them from Mhyo infection. Direct incorporation of P102 DNA sequences into host cells may also be used to introduce the sequences into animal cells for expression of antigen in vivo.

The above description, drawings and examples are only illustrative of preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. An isolated protein comprising the amino acid sequence of P102 having SEQ ID NO: 2.
2. A DNA encoding the protein of claim 1.
3. The DNA of claim 2, wherein said DNA is operatively linked to at least one control sequence.
4. A vector comprising the DNA of claim 2 wherein said vector is capable of expressing a protein encoded by said DNA.
5. A bacterial host cell transformed with the DNA of claim 2 wherein said bacterial host cell is capable of expressing a protein encoded by said DNA.
6. An immunogenic composition comprising the protein of claim 1.
7. An immunogenic composition comprising an immunogenic fragment of the protein of claim 1.
8. A DNA encoding an immunogenic fragment of the protein of claim 1.
9. The DNA of claim 8, wherein said DNA is operatively linked to at least one control sequence.
10. A vector comprising the DNA of claim 8 wherein said vector is capable of expressing a protein encoded by said DNA.
11. A bacterial host cell transformed with the DNA of claim 8 wherein said bacterial host cell is capable of expressing a protein encoded by said DNA.
12. A method of causing an immune response in an animal comprising the step of administering the protein of claim 1 to said animal.
13. A method of causing an immune response in an animal comprising the step of administering the protein of claim 7 to said animal.

14. A method for detecting the presence of P102 antibodies in a test sample, comprising the steps of:
- providing a test sample suspected of containing P102 antibodies;
- adding a quantity of the protein of claim 1 to the test sample, the quantity being sufficient to produce a detectable level of binding activity by anti-P102 antibodies in the test sample; and
- detecting the presence of P102 antibodies bound to said protein in the test sample.

15. A method for detecting the presence of P102 antibodies in a test sample, comprising the steps of:
- providing a test sample suspected of containing P102 antibodies;
- adding a quantity of an immunogenic fragment of the protein of claim 1 to the test sample, the quantity being sufficient to produce a detectable level of binding activity by anti-P102 antibodies in the test sample; and
- detecting the presence of P102 antibodies bound to said protein in the test sample.

16. A diagnostic kit for detecting the presence of P102 antibodies in a test sample, comprising:
- a carrier and at least one container, wherein said at least one container contains the protein of claim 1.

17. A diagnostic kit for detecting the presence of P102 antibodies in a test sample, comprising:
- a carrier and at least one container, wherein said at least one container contains an immunogenic fragment of the protein of claim 1.

* * * * *

SEQUENCE LISTING

<160> NUMBER OF SEQ ID NOS: 10

<210> SEQ ID NO 1
<211> LENGTH: 2760
<212> TYPE: DNA
<213> ORGANISM: Mycoplasma hyopneumoniae

```
<220> FEATURE:
<221> NAME/KEY: CDS
<222> LOCATION: (25)..(2736)
<220> FEATURE:
<221> NAME/KEY: opal codon
<222> LOCATION: (various positions throughout the sequence)
<223> OTHER INFORMATION: opal codon (tga) as coding for tryptophan

<400> SEQUENCE: 1
ataaaacccg gaggtattta tcct atg aag tta gca aaa tta ctt aaa aaa         51
                          Met Lys Leu Ala Lys Leu Leu Lys Lys
                           1               5 cct ttt tga tta ata aca aca att gcc gga att agt ctt agt tta tca        99
Pro Phe trp Leu Ile Thr Thr Ile Ala Gly Ile Ser Leu Ser Leu Ser
 10              15                  20                  25 gcc gct gtt ggt aca gtt gtc gga att aat tct tat aat aaa tca tat       147
Ala Ala Val Gly Thr Val Val Gly Ile Asn Ser Tyr Asn Lys Ser Tyr
                 30                  35                  40 tat tct tat cta aat cag atc ccg agt cag cta aaa gta gca aaa aat       195
Tyr Ser Tyr Leu Asn Gln Ile Pro Ser Gln Leu Lys Val Ala Lys Asn
             45                  50                  55 gct aaa att agt cag gaa aaa ttt gat tca att gtt tta aat ctt aaa       243
Ala Lys Ile Ser Gln Glu Lys Phe Asp Ser Ile Val Leu Asn Leu Lys
         60                  65                  70 att aaa gat aat ttt aaa aaa tga tcg gca aaa aca gtt tta act gct       291
Ile Lys Asp Asn Phe Lys Lys trp Ser Ala Lys Thr Val Leu Thr Ala
     75                  80                  85 gcc aaa agt gat ctt tat cgt tat aat ctt gtt tct gct ttt gat tta       339
Ala Lys Ser Asp Leu Tyr Arg Tyr Asn Leu Val Ser Ala Phe Asp Leu
 90                  95                 100                 105 agt gaa cta ata aac aat gat tat tta gta agt ttt gat ctt gaa aat       387
Ser Glu Leu Ile Asn Asn Asp Tyr Leu Val Ser Phe Asp Leu Glu Asn
                110                 115                 120 gca gta gtt gat caa aat tca att aaa aat gtt gtt att tat gca aaa       435
Ala Val Val Asp Gln Asn Ser Ile Lys Asn Val Val Ile Tyr Ala Lys
            125                 130                 135 tct gat aag gat caa ata act tat tca aaa caa att gta ctt aaa ggc       483
Ser Asp Lys Asp Gln Ile Thr Tyr Ser Lys Gln Ile Val Leu Lys Gly
        140                 145                 150 ttt gga aat aca gaa caa gct aga act aat ttt gat ttt agt caa att       531
Phe Gly Asn Thr Glu Gln Ala Arg Thr Asn Phe Asp Phe Ser Gln Ile
    155                 160                 165 gat tca agc aag tct ttt gtt gat ctt tca aga gca aat cta act ttg       579
Asp Ser Ser Lys Ser Phe Val Asp Leu Ser Arg Ala Asn Leu Thr Leu
170                 175                 180                 185 atg gaa ttc caa att ttg ctt gcc caa aat ttt gaa aat gaa aga gga       627
Met Glu Phe Gln Ile Leu Leu Ala Gln Asn Phe Glu Asn Glu Arg Gly
                190                 195                 200 agt aat tga ttt tca cga ctt gaa aga gct ttg gtt gca tca aaa gcg       675
Ser Asn trp Phe Ser Arg Leu Glu Arg Ala Leu Val Ala Ser Lys Ala
            205                 210                 215 agt ctt tca ctt tat aat tcc tta gga gaa ccc gta ttt tta ggc cca       723
Ser Leu Ser Leu Tyr Asn Ser Leu Gly Glu Pro Val Phe Leu Gly Pro
        220                 225                 230 gat tat caa tta gac cca gtt ttg gac cga aaa aaa tta tta act ttg       771
Asp Tyr Gln Leu Asp Pro Val Leu Asp Arg Lys Lys Leu Leu Thr Leu
    235                 240                 245 tta aat aaa gat gga aaa tta gtt ctt gga ctt aat tta gtg caa att       819
Leu Asn Lys Asp Gly Lys Leu Val Leu Gly Leu Asn Leu Val Gln Ile
250                 255                 260                 265 tca act aaa aaa act atg aat tta aat ctt gaa gtt cgc ggc gcg att       867
```

-continued

```
Ser Thr Lys Lys Thr Met Asn Leu Asn Leu Glu Val Arg Gly Ala Ile
            270                 275                 280 tca aat cag gaa att tct aaa att cta aaa tcc tga ctt gaa aca aat      915
Ser Asn Gln Glu Ile Ser Lys Ile Leu Lys Ser trp Leu Glu Thr Asn
            285                 290                 295 ctt caa ggc aaa tta aaa acc aaa gat gat ttg caa atg gca cta gta      963
Leu Gln Gly Lys Leu Lys Thr Lys Asp Asp Leu Gln Met Ala Leu Val
            300                 305                 310 aaa gat aaa att agc ctc tct gat tat tga tat gga tct ccg aat tca     1011
Lys Asp Lys Ile Ser Leu Ser Asp Tyr trp Tyr Gly Ser Pro Asn Ser
            315                 320                 325 aaa gta aat aca tcc caa att tta aca aaa agt aaa gaa ttt aaa gat     1059
Lys Val Asn Thr Ser Gln Ile Leu Thr Lys Ser Lys Glu Phe Lys Asp
330                 335                 340                 345 ctt ttt gat tta agt gag aca aat ttt ttt ctt aat acc aaa atc gga     1107
Leu Phe Asp Leu Ser Glu Thr Asn Phe Phe Leu Asn Thr Lys Ile Gly
            350                 355                 360 act gtc tat tta agt att att ccc aaa ctt tta gat cca agt cag att     1155
Thr Val Tyr Leu Ser Ile Ile Pro Lys Leu Leu Asp Pro Ser Gln Ile
            365                 370                 375 tct gtt gtt gat aag aaa aaa cta gtt gaa aat caa aaa att cgc ttt     1203
Ser Val Val Asp Lys Lys Lys Leu Val Glu Asn Gln Lys Ile Arg Phe
            380                 385                 390 gaa att act gct tct tta aaa cga aaa gct att gat aaa aaa ttt atc     1251
Glu Ile Thr Ala Ser Leu Lys Arg Lys Ala Ile Asp Lys Lys Phe Ile
395                 400                 405 atc cag gat ctt cca gtt ttt gtt gat cta aaa gtt gat ttt aat aaa     1299
Ile Gln Asp Leu Pro Val Phe Val Asp Leu Lys Val Asp Phe Asn Lys
410                 415                 420                 425 tac caa gcc gct gtt gcc caa atg ttt gga acg ata aaa gca gtt aaa     1347
Tyr Gln Ala Ala Val Ala Gln Met Phe Gly Thr Ile Lys Ala Val Lys
            430                 435                 440 gaa ttt tca atg cct gaa gat caa gat gca aaa act tta tcc tca aat     1395
Glu Phe Ser Met Pro Glu Asp Gln Asp Ala Lys Thr Leu Ser Ser Asn
            445                 450                 455 gaa ata aaa cag cga gtt gat cga ctt ttt gaa cta gca aaa aca gtg     1443
Glu Ile Lys Gln Arg Val Asp Arg Leu Phe Glu Leu Ala Lys Thr Val
            460                 465                 470 act aat ttg gaa aat cca agt gaa gaa gtt ctt aaa agc att tat tta     1491
Thr Asn Leu Glu Asn Pro Ser Glu Glu Val Leu Lys Ser Ile Tyr Leu
            475                 480                 485 tta aat acg gga aaa tat tta gtc gac caa gac cag gaa aaa gta aaa     1539
Leu Asn Thr Gly Lys Tyr Leu Val Asp Gln Asp Gln Glu Lys Val Lys
490                 495                 500                 505 caa gag cta aaa acc gtg att gag ggc tta aaa tca aag gca aat act     1587
Gln Glu Leu Lys Thr Val Ile Glu Gly Leu Lys Ser Lys Ala Asn Thr
            510                 515                 520 caa aaa aca gaa aaa aat agc ccc aca caa ccg aaa aaa cca gag gtt     1635
Gln Lys Thr Glu Lys Asn Ser Pro Thr Gln Pro Lys Lys Pro Glu Val
            525                 530                 535 tca cta gct aaa aca aca gaa aat tca gca aaa aca gtc aag gta agc     1683
Ser Leu Ala Lys Thr Thr Glu Asn Ser Ala Lys Thr Val Lys Val Ser
            540                 545                 550 act ttt gca gaa gaa gct aag ggt caa agt caa agt cag caa aca caa     1731
Thr Phe Ala Glu Glu Ala Lys Gly Gln Ser Gln Ser Gln Gln Thr Gln
            555                 560                 565 cca gtt tcc act tca tcg cct caa act agt caa aat tca ctt cct aat     1779
Pro Val Ser Thr Ser Ser Pro Gln Thr Ser Gln Asn Ser Leu Pro Asn
570                 575                 580                 585
```

```
tcc aca agc agc tca aat tct gta tta gaa aat gaa aaa ttt ggg aca      1827
Ser Thr Ser Ser Ser Asn Ser Val Leu Glu Asn Glu Lys Phe Gly Thr
                590                 595                 600 agc att tga aca gct ttt aat ttc gct aat att tat aat ctt gaa aat      1875
Ser Ile trp Thr Ala Phe Asn Phe Ala Asn Ile Tyr Asn Leu Glu Asn
                605                 610                 615 aca aaa agc gaa tat gag atc tca act tta gga aat aag cta ttt ttt      1923
Thr Lys Ser Glu Tyr Glu Ile Ser Thr Leu Gly Asn Lys Leu Phe Phe
                620                 625                 630 gat ttt aaa tta gtt gat aaa act aat caa aat cta att ttg gct cag      1971
Asp Phe Lys Leu Val Asp Lys Thr Asn Gln Asn Leu Ile Leu Ala Gln
            635                 640                 645 tcc aaa att agt ctt aat aat att att aat tct aat aaa tct gcc tat      2019
Ser Lys Ile Ser Leu Asn Asn Ile Ile Asn Ser Asn Lys Ser Ala Tyr
650                 655                 660                 665 gat ata att aag aaa ttc aat ccc gat gtg ttt tta gat gga aca att      2067
Asp Ile Ile Lys Lys Phe Asn Pro Asp Val Phe Leu Asp Gly Thr Ile
                670                 675                 680 aat tat caa aat caa gga aaa gat aaa aaa gaa ttt atc cta aaa gat      2115
Asn Tyr Gln Asn Gln Gly Lys Asp Lys Lys Glu Phe Ile Leu Lys Asp
                685                 690                 695 tta agt gat aat aaa tta ata ttt aaa tca gaa gat gca att caa act      2163
Leu Ser Asp Asn Lys Leu Ile Phe Lys Ser Glu Asp Ala Ile Gln Thr
                700                 705                 710 gat caa ggt tta gag cta aag aaa cct ttg aaa tta cag tca aaa tcg      2211
Asp Gln Gly Leu Glu Leu Lys Lys Pro Leu Lys Leu Gln Ser Lys Ser
            715                 720                 725 tct aat cca gaa aaa gaa ata tca act tct tta tat acc gga gca att      2259
Ser Asn Pro Glu Lys Glu Ile Ser Thr Ser Leu Tyr Thr Gly Ala Ile
730                 735                 740                 745 tat tta gtt ttt gat gca aaa aat att tcc gat ggt aat tgg att aat      2307
Tyr Leu Val Phe Asp Ala Lys Asn Ile Ser Asp Gly Asn Trp Ile Asn
                750                 755                 760 ctt tta gcc gat aga aaa gga aaa ggg ctt gta att aaa gtt caa aat      2355
Leu Leu Ala Asp Arg Lys Gly Lys Gly Leu Val Ile Lys Val Gln Asn
                765                 770                 775 tca aat aat aat gta cct aaa acc aaa gaa att gtt gag aat ggt acc      2403
Ser Asn Asn Asn Val Pro Lys Thr Lys Glu Ile Val Glu Asn Gly Thr
                780                 785                 790 tat tta tat gaa att ctt gct ggc aag gat tcg att aag gta aat tct      2451
Tyr Leu Tyr Glu Ile Leu Ala Gly Lys Asp Ser Ile Lys Val Asn Ser
795                 800                 805 tat ttt ttt cca aca aag tac cca aaa cgt gta aaa cgt ctt aaa ttc      2499
Tyr Phe Phe Pro Thr Lys Tyr Pro Lys Arg Val Lys Arg Leu Lys Phe
810                 815                 820                 825 gag att aac cct aaa gac acc ttg cca aat ttc ttt act tta gaa tga      2547
Glu Ile Asn Pro Lys Asp Thr Leu Pro Asn Phe Phe Thr Leu Glu trp
                830                 835                 840 ttt cat ctt gat tgg tat caa atc ggc cca ggc gaa caa aat aaa aaa      2595
Phe His Leu Asp Trp Tyr Gln Ile Gly Pro Gly Glu Gln Asn Lys Lys
            845                 850                 855 cca caa caa aac gct aaa aaa gaa cct aca att ata tta aaa acg ctg      2643
Pro Gln Gln Asn Ala Lys Lys Glu Pro Thr Ile Ile Leu Lys Thr Leu
                860                 865                 870 gca ata ttt aat gat aaa tca ttt gca gag aaa gga agt tta aca aaa      2691
Ala Ile Phe Asn Asp Lys Ser Phe Ala Glu Lys Gly Ser Leu Thr Lys
            875                 880                 885 aga agt gaa tta att aac ggg ttg att aga aac tat gtt aaa aag          2736
Arg Ser Glu Leu Ile Asn Gly Leu Ile Arg Asn Tyr Val Lys Lys
890                 895                 900
```
taacgatcaa attttgtta aaaa                                                                                          2760

<210> SEQ ID NO 2
<211> LENGTH: 904
<212> TYPE: PRT
<213> ORGANISM: Mycoplasma hyopneumoniae

<400> SEQUENCE: 2

Met Lys Leu Ala Lys Leu Leu Lys Lys P

```
Pro Lys Leu Leu Asp Pro Ser Gln Ile Ser Val Asp Lys Lys
    370                 375                 380

Leu Val Glu Asn Gln Lys Ile Arg Phe Glu Ile Thr Ala Ser Leu Lys
385                 390                 395                 400

Arg Lys Ala Ile Asp Lys Lys Phe Ile Ile Gln Asp Leu Pro Val Phe
                    405                 410                 415

Val Asp Leu Lys Val Asp Phe Asn Lys Tyr Gln Ala Ala Val Ala Gln
                420                 425                 430

Met Phe Gly Thr Ile Lys Ala Val Lys Glu Phe Ser Met Pro Glu Asp
            435                 440                 445

Gln Asp Ala Lys Thr Leu Ser Ser Asn Glu Ile Lys Gln Arg Val Asp
        450                 455                 460

Arg Leu Phe Glu Leu Ala Lys Thr Val Thr Asn Leu Glu Asn Pro Ser
465                 470                 475                 480

Glu Glu Val Leu Lys Ser Ile Tyr Leu Leu Asn Thr Gly Lys Tyr Leu
                    485                 490                 495

Val Asp Gln Asp Gln Glu Lys Val Lys Gln Glu Leu Lys Thr Val Ile
                500                 505                 510

Glu Gly Leu Lys Ser Lys Ala Asn Thr Gln Lys Thr Glu Lys Asn Ser
            515                 520                 525

Pro Thr Gln Pro Lys Lys Pro Glu Val Ser Leu Ala Lys Thr Thr Glu
        530                 535                 540

Asn Ser Ala Lys Thr Val Lys Val Ser Thr Phe Ala Glu Glu Ala Lys
545                 550                 555                 560

Gly Gln Ser Gln Ser Gln Gln Thr Gln Pro Val Ser Thr Ser Ser Pro
                    565                 570                 575

Gln Thr Ser Gln Asn Ser Leu Pro Asn Ser Thr Ser Ser Asn Ser
                580                 585                 590

Val Leu Glu Asn Glu Lys Phe Gly Thr Ser Ile trp Thr Ala Phe Asn
            595                 600                 605

Phe Ala Asn Ile Tyr Asn Leu Glu Asn Thr Lys Ser Glu Tyr Glu Ile
        610                 615                 620

Ser Thr Leu Gly Asn Lys Leu Phe Phe Asp Phe Lys Leu Val Asp Lys
625                 630                 635                 640

Thr Asn Gln Asn Leu Ile Leu Ala Gln Ser Lys Ile Ser Leu Asn Asn
                    645                 650                 655

Ile Ile Asn Ser Asn Lys Ser Ala Tyr Asp Ile Ile Lys Lys Phe Asn
                660                 665                 670

Pro Asp Val Phe Leu Asp Gly Thr Ile Asn Tyr Gln Asn Gln Gly Lys
            675                 680                 685

Asp Lys Lys Glu Phe Ile Leu Lys Asp Leu Ser Asp Asn Lys Leu Ile
        690                 695                 700

Phe Lys Ser Glu Asp Ala Ile Gln Thr Asp Gln Gly Leu Glu Leu Lys
705                 710                 715                 720

Lys Pro Leu Lys Leu Gln Ser Ser Ser Asn Pro Glu Lys Glu Ile
                    725                 730                 735

Ser Thr Ser Leu Tyr Thr Gly Ala Ile Tyr Leu Val Phe Asp Ala Lys
                740                 745                 750

Asn Ile Ser Asp Gly Asn Trp Ile Asn Leu Leu Ala Asp Arg Lys Gly
            755                 760                 765

Lys Gly Leu Val Ile Lys Val Gln Asn Ser Asn Asn Val Pro Lys
        770                 775                 780
```

```
Thr Lys Glu Ile Val Glu Asn Gly Thr Tyr Leu Tyr Glu Ile Leu Ala
785                 790                 795                 800

Gly Lys Asp Ser Ile Lys Val Asn Ser Tyr Phe Phe Pro Thr Lys Tyr
                805                 810                 815

Pro Lys Arg Val Lys Arg Leu Lys Phe Glu Ile Asn Pro Lys Asp Thr
                820                 825                 830

Leu Pro Asn Phe Phe Thr Leu Glu trp Phe His Leu Asp Trp Tyr Gln
                835                 840                 845

Ile Gly Pro Gly Glu Gln Asn Lys Lys Pro Gln Gln Asn Ala Lys Lys
        850                 855                 860

Glu Pro Thr Ile Ile Leu Lys Thr Leu Ala Ile Phe Asn Asp Lys Ser
865                 870                 875                 880

Phe Ala Glu Lys Gly Ser Leu Thr Lys Arg Ser Glu Leu Ile Asn Gly
                885                 890                 895

Leu Ile Arg Asn Tyr Val Lys Lys
            900

<210> SEQ ID NO 3
<211> LENGTH: 361
<212> TYPE: PRT
<213> ORGANISM: protein encoded by a clone of Mycoplasma hyopneumoniae

<400> SEQUENCE: 3

Met Lys Leu Ala Lys Leu Leu Lys Lys Pro Phe Trp Leu Ile Thr Thr
1               5                   10                  15

Ile Ala Gly Ile Ser Leu Ser Leu Ser Ala Ala Val Gly Thr Val Val
                20                  25                  30

Gly Ile Asn Ser Tyr Asn Lys Ser Tyr Tyr Ser Tyr Leu Asn Gln Ile
            35                  40                  45

Pro Ser Gln Leu Lys Val Ala Lys Asn Ala Lys Ile Ser Gln Glu Lys
        50                  55                  60

Phe Asp Ser Ile Val Leu Asn Leu Lys Ile Lys Asp Asn Phe Lys Lys
65                  70                  75                  80

Trp Ser Ala Lys Thr Val Leu Thr Ala Ala Lys Ser Asp Leu Tyr Arg
                85                  90                  95

Tyr Asn Leu Val Ser Ala Phe Asp Leu Ser Glu Leu Ile Asn Asn Asp
                100                 105                 110

Tyr Leu Val Ser Phe Asp Leu Glu Asn Ala Val Val Asp Gln Asn Ser
            115                 120                 125

Ile Lys Asn Val Val Ile Tyr Ala Lys Ser Asp Lys Asp Gln Ile Thr
        130                 135                 140

Tyr Ser Lys Gln Ile Val Leu Lys Gly Phe Gly Asn Thr Glu Gln Ala
145                 150                 155                 160

Arg Thr Asn Phe Asp Phe Ser Gln Ile Asp Ser Ser Lys Ser Phe Val
                165                 170                 175

Asp Leu Ser Arg Ala Asn Leu Thr Leu Thr Glu Phe Asn Ser Lys Val
                180                 185                 190

Asn Thr Ser Gln Ile Leu Thr Lys Ser Lys Glu Phe Lys Asp Leu Phe
            195                 200                 205

Asp Leu Ser Glu Thr Asn Phe Phe Leu Asn Thr Lys Ile Gly Thr Val
        210                 215                 220

Tyr Leu Ser Ile Ile Pro Lys Leu Leu Asp Pro Ser Gln Ile Ser Val
225                 230                 235                 240

Val Asp Lys Lys Lys Leu Val Glu Asn Gln Lys Ile Arg Phe Glu Ile
                245                 250                 255
```

```
Thr Ala Ser Leu Lys Arg Lys Ala Ile Asp Lys Lys Phe Ile Ile Gln
            260                 265                 270

Asp Leu Pro Val Phe Val Asp Leu Lys Val Asp Phe Asn Lys Tyr Gln
            275                 280                 285

Ala Ala Val Ala Gln Met Phe Gly Thr Ile Lys Ala Val Lys Glu Phe
            290                 295                 300

Ser Met Pro Glu Asp Gln Asp Ala Lys Thr Leu Ser Ser Asn Glu Ile
305                 310                 315                 320

Lys Gln Arg Val Asp Arg Leu Phe Glu Leu Ala Lys Thr Val Thr Asn
                325                 330                 335

Leu Glu Asn Pro Ser Glu Glu Val Leu Lys Ser Ile Tyr Leu Leu Asn
            340                 345                 350

Thr Gly Lys Tyr Leu Val Asp Gln Asp
            355                 360

<210> SEQ ID NO 4
<211> LENGTH: 495
<212> TYPE: PRT
<213> ORGANISM: protein encoded by a clone of Mycoplasma hyopneumoniae

<400> SEQUENCE: 4

Leu Leu Lys Lys Pro Phe Trp Leu Ile Thr Thr Ile Ala Gly Ile Ser
  1               5                  10                  15

Leu Ser Leu Ser Ala Ala Val Gly Ile Val Gly Ile Asn Ser Tyr
             20                  25                  30

Asn Lys Ser Tyr Tyr Ser Tyr Leu Asn Glu Asn Pro Ser Gln Leu Lys
             35                  40                  45

Thr Thr Lys Thr Thr Lys Ile Ser Gln Gln Asp Phe Asp Lys Ile Val
         50                  55                  60

Ser Asn Leu Lys Ile Arg Asp Asn Phe Lys Lys Ile Ser Ala Lys Thr
 65                  70                  75                  80

Ala Leu Ser Ala Val Lys Asn Asp Leu Tyr Arg Tyr Asp Leu Val Arg
                 85                  90                  95

Ala Phe Glu Phe Ser Ser Leu Glu Thr Asn Asn Tyr Gln Ile Ser Phe
            100                 105                 110

Asp Leu Glu Asn Ala Val Val Asp Gln Asn Ser Ile Lys Asn Val Val
            115                 120                 125

Ile Tyr Ala Lys Ser Asp Lys Asp Gln Ile Thr Tyr Ser Lys Gln Ile
        130                 135                 140

Val Leu Lys Gly Phe Gly Asn Thr Glu Gln Ala Arg Thr Asn Phe Asp
145                 150                 155                 160

Phe Ser Gln Ile Asp Ser Ser Lys Ser Phe Val Asp Leu Ser Arg Ala
                165                 170                 175

Asn Leu Thr Leu Thr Glu Phe Gln Ile Leu Leu Ala Gly Asn Phe Glu
            180                 185                 190

Asn Glu Arg Gly Ser Asn Trp Phe Ser Arg Leu Glu Arg Ala Leu Val
        195                 200                 205

Ala Ser Lys Ala Ser Leu Ser Leu Tyr Asn Ser Leu Gly Glu Pro Val
210                 215                 220

Phe Leu Gly Pro Asp Tyr Gln Leu Asp Pro Val Leu Asp Arg Lys Lys
225                 230                 235                 240

Leu Leu Thr Leu Leu Asn Lys Asp Gly Lys Leu Val Leu Gly Leu Asn
                245                 250                 255

Leu Val Gln Ile Ser Thr Lys Lys Thr Met Asn Leu Asn Leu Glu Val
```

-continued

```
                260                 265                 270
Arg Gly Ala Ile Ser Asn Gln Glu Ile Ser Lys Ile Leu Lys Ser Trp
            275                 280                 285

Leu Glu Thr Asn Leu Gln Gly Lys Leu Lys Thr Lys Asp Asp Leu Gln
        290                 295                 300

Met Ala Leu Val Lys Asp Lys Ile Ser Leu Ser Asp Tyr Trp Tyr Gly
305                 310                 315                 320

Ser Pro Asn Ser Lys Val Asn Thr Ser Gln Ile Leu Thr Lys Ser Lys
                325                 330                 335

Glu Phe Lys Asp Leu Phe Asp Leu Ser Glu Thr Asn Phe Phe Leu Asn
            340                 345                 350

Thr Lys Ile Gly Thr Val Tyr Leu Ser Ile Ile Pro Lys Leu Leu Asp
        355                 360                 365

Pro Ser Gln Ile Ser Val Val Asp Lys Lys Leu Val Glu Asn Gln
370                 375                 380

Lys Ile Arg Phe Glu Ile Thr Ala Ser Leu Lys Arg Lys Ala Ile Asp
385                 390                 395                 400

Lys Lys Phe Ile Ile Gln Asp Leu Pro Val Phe Val Asp Leu Lys Val
                405                 410                 415

Asp Phe Asn Lys Tyr Gln Ala Ala Val Ala Gln Met Phe Gly Thr Ile
            420                 425                 430

Lys Ala Val Lys Glu Phe Ser Met Pro Glu Asp Gln Asp Ala Lys Thr
        435                 440                 445

Leu Ser Ser Asn Glu Ile Lys Gln Arg Val Asp Arg Leu Phe Glu Leu
    450                 455                 460

Ala Lys Thr Val Thr Asn Leu Glu Asn Pro Ser Glu Val Leu Lys
465                 470                 475                 480

Ser Ile Tyr Leu Leu Asn Thr Gly Lys Tyr Leu Val Asp Gln Asp
                485                 490                 495

<210> SEQ ID NO 5
<211> LENGTH: 191
<212> TYPE: PRT
<213> ORGANISM: protein encoded by a clone of Mycoplasma hyopneumoniae

<400> SEQUENCE: 5

Met Lys Leu Ala Lys Leu Leu Lys Lys Pro Phe Trp Leu Ile Thr Thr
1               5                   10                  15

Ile Ala Gly Ile Ser Leu Ser Leu Ser Ala Ala Val Gly Ile Val Val
            20                  25                  30

Gly Ile Asn Ser Tyr Asn Lys Ser Tyr Tyr Ser Tyr Leu Asn Glu Asn
        35                  40                  45

Pro Ser Gln Leu Lys Thr Thr Lys Thr Thr Lys Ile Ser Gln Gln Asp
    50                  55                  60

Phe Asp Lys Ile Val Ser Asn Leu Lys Ile Arg Asp Asn Phe Lys Lys
65                  70                  75                  80

Ile Ser Ala Lys Thr Ala Leu Ser Ala Val Lys Asn Asp Leu Tyr Arg
                85                  90                  95

Tyr Asp Leu Val Arg Ala Phe Glu Phe Ser Ser Leu Glu Thr Asn Asn
            100                 105                 110

Tyr Gln Ile Ser Phe Asp Leu Glu Asn Ala Val Val Asp Gln Asn Ser
        115                 120                 125

Ile Lys Asn Val Leu Val Phe Ala Lys Ser Glu Lys Asp Gln Val Thr
    130                 135                 140
```

-continued

```
Tyr Ser Lys Gln Ile Glu Leu Lys Gly Phe Ala Gln Asp Asp Glu Ala
145                 150                 155                 160

Ala Gly Asp Leu Val Lys Phe Gln Ile Asp Gln Arg Lys Ser Phe Val
                165                 170                 175

Asn Leu Tyr Lys Phe Asp Tyr Ser Phe Ser Glu Phe Gln Arg Ile
            180                 185                 190

<210> SEQ ID NO 6
<211> LENGTH: 22
<212> TYPE: DNA
<213> ORGANISM: primer

<400> SEQUENCE: 6
atataaacaa cgaattatct cc                                        22

<210> SEQ ID NO 7
<211> LENGTH: 18
<212> TYPE: DNA
<213> ORGANISM: primer

<400> SEQUENCE: 7
taagttatac cataaacg                                             18

<210> SEQ ID NO 8
<211> LENGTH: 21
<212> TYPE: DNA
<213> ORGANISM: primer

<400> SEQUENCE: 8
aaggtaaaag agaagaagta g                                         21

<210> SEQ ID NO 9
<211> LENGTH: 21
<212> TYPE: DNA
<213> ORGANISM: primer

<400> SEQUENCE: 9
ttgtaagtga aaagccagta t                                         21

<210> SEQ ID NO 10
<211> LENGTH: 21
<212> TYPE: DNA
<213> ORGANISM: primer

<400> SEQUENCE: 10
gcggctgcta aactaagact a                                         21
```